US010619164B2

(12) United States Patent
Tolstorukov et al.

(10) Patent No.: US 10,619,164 B2
(45) Date of Patent: Apr. 14, 2020

(54) **YEAST PROMOTERS FROM *PICHIA PASTORIS***

(71) Applicant: KECK GRADUATE INSTITUTE OF APPLIED LIFE SCIENCES, Claremont, CA (US)

(72) Inventors: Ilya I. Tolstorukov, Claremont, CA (US); James M. Cregg, Claremont, CA (US)

(73) Assignee: Keck Graduate Institute of Applied Life Sciences, Claremont, CA (US)

( * ) Notice: Subject to any disclaimer, the term of this patent is extended or adjusted under 35 U.S.C. 154(b) by 0 days.

(21) Appl. No.: 14/773,474

(22) PCT Filed: Mar. 7, 2014

(86) PCT No.: PCT/US2014/022135
§ 371 (c)(1),
(2) Date: Sep. 8, 2015

(87) PCT Pub. No.: WO2014/138703
PCT Pub. Date: Sep. 12, 2014

(65) Prior Publication Data

US 2016/0097053 A1 Apr. 7, 2016

Related U.S. Application Data

(60) Provisional application No. 61/774,982, filed on Mar. 8, 2013.

(51) Int. Cl.
*C12N 1/19* (2006.01)
*C12N 15/81* (2006.01)

(52) U.S. Cl.
CPC ........... *C12N 15/815* (2013.01); *C12N 15/81* (2013.01)

(58) Field of Classification Search
None
See application file for complete search history.

(56) References Cited

U.S. PATENT DOCUMENTS

| | | | | |
|---|---|---|---|---|
| 6,451,572 | B1 | 9/2002 | Lei | |
| 6,841,370 | B1 | 1/2005 | Lei | |
| 6,974,690 | B2 | 12/2005 | Lei | |
| 7,078,035 | B2 | 7/2006 | Short et al. | |
| 7,138,260 | B2 | 11/2006 | Lanahan et al. | |
| 7,320,876 | B2 | 1/2008 | Webel et al. | |
| 9,150,870 | B2 * | 10/2015 | Mattanovich | C12N 15/815 |
| 2005/0164259 | A1 | 7/2005 | Morgan et al. | |
| 2008/0108108 | A1 | 5/2008 | Cregg | |
| 2008/0286415 | A1 * | 11/2008 | Lassen | A23J 3/346 426/63 |
| 2011/0258714 | A1 | 10/2011 | De Maria et al. | |
| 2012/0100581 | A1 | 4/2012 | Gramatikova et al. | |
| 2014/0011236 | A1 * | 1/2014 | Davidson | C12P 21/00 435/69.1 |
| 2014/0274761 | A1 * | 9/2014 | Mattanovich | C12N 15/815 506/9 |
| 2016/0024511 | A1 | 1/2016 | Tolstorukov | |

FOREIGN PATENT DOCUMENTS

| | | | | |
|---|---|---|---|---|
| CN | 1802433 A | | 6/2006 | |
| CN | 101014704 A | | 8/2007 | |
| CN | 101460612 | | 6/2009 | |
| CN | 102994501 A | * | 3/2013 | |
| EP | 2199389 | | 6/2010 | |
| EP | 2862933 | | 4/2015 | |
| EP | 2964765 | | 1/2016 | |
| WO | WO 99/67398 | | 12/1999 | |
| WO | WO 2007/112739 | | 10/2007 | |
| WO | WO 2008/090211 | | 7/2008 | |
| WO | WO 2008/128701 | | 10/2008 | |
| WO | WO 2010/004042 | | 1/2010 | |
| WO | WO 2012129036 A2 | * | 9/2012 | C12P 21/00 |
| WO | WO 2014/138703 | | 3/2014 | |
| WO | WO-2014066374 A1 | * | 5/2014 | |
| WO | 20140138679 | | 9/2014 | |

OTHER PUBLICATIONS

Liang et al., Identification and characterization of PGCW14, Biotechnol. Lett., Jun. 2013, 35, 1865-71.*
Xuanwei et al., Application of Pichia pastoris original constitutive strong promoter GCW14 in Candidn Antarctic lipase B in yeast surface display, Biotechnol. Bulletin, Apr. 2013, 129-35.*
Struhl, Fundamentally different logic of gene regulation in eukaryotes and prokaryotes, Cell, 1999, 98,1-4.*
Ohi et al., The positive and negative cis-acting elements for methanol regulation in the Pichia pastoris AOX2 gene, Mol. Gen. Genet ., 1994, 243, 489-99.*
Zhang et al., Key regulatory elements of a strong constitutive promoter, PGCW14, from Pichia pastoris, Biotechnol. Lett., 2013, 35, 2113-19.*
U.S. Appl. No. 61/774, 982, filed Mar. 8, 2013, Tolstorukov et al.
De Schutter et al., Genome Sequence of the Recombinant Protein Production Host Pichia Pastoris. Nat Biotechnol., (2009), 27(6): pp. 561-566.
International Search Report and Written Opinion for PCT/US2014/0022135, completed Jun. 6, 2014.

(Continued)

*Primary Examiner* — Robert B Mondesi
*Assistant Examiner* — Todd M Epstein
(74) *Attorney, Agent, or Firm* — Barnes & Thornburg LLP

(57) ABSTRACT

In accordance with the invention, isolated nucleic acids, expression methods, host cells, expression vectors, and DNA constructs for producing proteins, and proteins produced using the expression methods are described. More particularly, nucleic acids isolated from *Pichia pastoris* wherein the nucleic acids have promoter activity are described. The invention also relates to expression methods, host cells, expression vectors, and DNA constructs, for using the *Pichia pastoris* promoters to produce proteins, and to the proteins produced using the expression methods.

17 Claims, 12 Drawing Sheets

Specification includes a Sequence Listing.

(56) References Cited

OTHER PUBLICATIONS

Sambrook et al., Molecular Cloning: A Laboratory Manual, $3^{rd}$ Edition, Cold Spring Harbor Laboratory Press (2001). [Book reference—provided at Examiner's request].
Altschul et al., Basic Local Alignment Search Tool, J. Mol. Biol. 215: pp. 403-410, (1990).
Rodriguez et al., Site-directed mutagenesis improves catalytic efficiency and thermostability of *Escherichia coli*pH 2.5 acid phosphatase/phytase expressed in Pichia pastoris, *Arch. of Biochem. and Biophys*. 382: 105-112, (2000).
GenBank Id No. FN392319.1 from De Schutter, K., "Genome Sequence of the Recombinant Protein Production Host Pichia Pastoris," Nature Biotechnol., 2009, 27, 561-566.
GenBank Id No. FN392322.1 from De Schutter, K., "Genome Sequence of the Recombinant Protein Production Host Pichia Pastoris," Nature Biotechnol., 2009, 27, 561-566.
Pichia pastoric Pp01g10900 promoter DNA sequence, XP002763247, retrieved from EBI accession No. GSN:BAA33112, Nov. 2012, 1 page.
Pichia pastoric Pp05g08520 promoter DNA sequence, XP002763248, retrieved from EBI accession No. GSN:BAA33112, Nov. 2012, 1 page.
Stadlmayr, G. et al., "Identification and characterization of novel Pichia pastoris promoters for heterologous protein production," Journal of Biotechnology, 2010, 150, 519-529.
Potvin, G. et al., "Bioprocess engineering aspects of heterologous protein production in Pichia pastoris: A review," Biochemical Engineering Journal, 2012, 64, 91-105.
Gene Bank accession No. M58708.
Macauley-Patrick et al., "Heterologous protein production using the Pichia pastoris expression system," Yeast, 2005, 22, 249-270.
International Search Report and Written Opinion prepared for PCT/US2014/022086, dated Aug. 11, 2014, 14 pages.
Genbank Id No. BAA33083, "Pichia pastoric Pp03g00990 methanol-inducible promoter DNA seq. 50," XP002761749, retrieved from EBI accession No. GSN:BAA33083, Nov. 2012, 1 page.
Tschopp, J. et al., "Expression of the IacZ gene from two methanol-regulated promoters in Pichia pastoris," Nucleic Acids Research, 1987, 15, 3859-3876.
Kuberl et al., "High-quality genome sequence of Pichia pastoris CBS7435," J Biotechnol. (Jul. 20, 2011) 154(4):312-20.
Rodriguez et al., AY496073.1, GenBank, pp. 1-2.
Hartner et al., Promoter library designed for fine-tuned gene expression in Pichia pastoris, 2008, Nucleic Acid Res., vol. 36, No. 12, e76.

* cited by examiner

Chr1-0469 PROMOTER SEQUENCE (SEQ ID NO: 1)

TGCCAGGATCTGACCACTACAAGAAGCGTAATTAAGTATTTATTATGTAGCTT
GAGGAATTGATTTCTAAAGGCCAAAGATGATGTAGAGCAATAGTAGAGTGAT
TAGCAAGTTTCTGAACATGTTTTGTGGTCGGGTATTAGGCGCCGTACCTCTGT
ATTTTTTTTTTTTGGCAGATGGGATGACCACTGTGCTTACATAATTTTCGATGG
GCCCTTTTGGAAACGACCACTCCTTCCGATCACGTAATACTAGGCGAGTATCA
CTACGCGTCGGTATCCGCATTTTAGCCGCTTTAACGACAAGGTCAGGGTAAAT
ACTGTGTTGCATGGGCGATGCCGTAGGATCTGGCCAACTTGGAACAGAGCAG
CCCACCGCGTAGGCAGCGCTTGGGACCAGTTTGTTAGCCAATCAGTTCCCCC
GTCTGAGTCCCTACACGCTCAGGCTTGCATGGATATGCATGAAAAATGTCAA
CTCAGTCGCACACAGGGATGCTGTTGTCGTGGTGAGAAAAAGCTAAAATAGC
AAACCCATAGCAATCGAGAGACTGTGATTGGAAGCAAAAGAACCAGGCATT
GACTAGGAAAGACTGACAAGAAAATTAGACGGTGCCAGTGGTATTTCATTGA
ATTGCACTGAACACGCCTCCCATTTCCTTCCCTCAATCCATTCAAAGGGCTAA
TTAAACCTTATCTCGGCCTACATTAGTTGTCATGGAAACGTCTCACTTTCTCTC
TGTGTCCCACAGTAGCGAGTAGGCGGAGAGACCAAAAATGGTCTCTCGGCCC
TAATCAAAACATCCTTTGTCGCGTTGTTTTCAGATCGATTCGCAATCTGAGAG
AAAAACAATAACACCAAAATAAAAAGCTTGGAAAAAGAAGACATGATTCAC
ATCCACTAGTAAAATATAAATACTCCTGCCGCCTCCCCCTTTCCTTTCTTCTTA
TTCCTCAACTCACTGTTTCAGTTTATTCCAACTACTTTCACTCACTTATCAAAA
ATG

FIG. 1

UPP PROMOTER SEQUENCE (SEQ ID NO: 2)

GGGTGAAAGCCAACCATCTTTGTTTCGGGGAACCGTGCTCGCCCCGTAAAGTTAA
TTTTTTTTTCCCGCGCAGCTTTAATCTTTCGGCAGAGAAGGCGTTTTCATCGTAGC
GTGGGAACAGAATAATCAGTTCATGTGCTATACAGGCACATGGCAGCAGTCACT
ATTTTGCTTTTTAACCTTAAAGTCGTTCATCAATCATTAACTGACCAATCAGATTT
TTTGCATTTGCCACTTATCTAAAAATACTTTTGTATCTCGCAGATACGTTCAGTGG
TTTCCAGGACAACACCCAAAAAAAGGTATCAATGCCACTAGGCAGTCGGTTTTAT
TTTTGGTCACCCACGCAAAGAAGCACCCACCTCTTTTAGGTTTTAAGTTGTGGGA
ACAGTAACACCGCCTAGAGCTTCAGGAAAAACCAGTACCTGTGACCGCAATTCA
CCATGATGCAGAATGTTAATTTAAACGAGTGCCAAATCAAGATTTCAACAGACA
AATCAATCGATCCATAGTTACCCATTCCAGCCTTTTCGTCGTCGAGCCTGCTTCAT
TCCTGCCTCAGGTGCATAACTTTGCATGAAAAGTCCAGATTAGGGCAGATTTTGA
GTTTAAAATAGGAAATATAAACAAATATACCGCGAAAAAGGTTTGTTTATAGCTT
TTCGCCTGGTGCCGTACGGTATAAATACATACTCTCCTCCCCCCCCTGGTTCTCTT
TTTCTTTTGTTACTTACATTTTACCGTTCCGTCACTCGCTTCACTCAACAACAAAA

FIG. 2

AOX1 PROMOTER SEQUENCE (SEQ ID NO: 3)

GATCTAACATCCAAAGACGAAAGGTTGAATGAAACCTTTTTGCCATCCGACATCC
ACAGGTCCATTCTCACACATAAGTGCCAAACGCAACAGGAGGGGATACACTAGC
AGCAGACCGTTGCAAACGCAGGACCTCCACTCCTCTTCTCCTCAACACCCACTTT
TGCCATCGAAAAACCAGCCCAGTTATTGGGCTTGATTGGAGCTCGCTCATTCCAA
TTCCTTCTATTAGGCTACTAACACCATGACTTTATTAGCCTGTCTATCCTGGCCCC
CCTGGCGAGGTTCATGTTTGTTTATTTCCGAATGCAACAAGCTCCGCATTACACC
CGAACATCACTCCAGATGAGGGCTTTCTGAGTGTGGGGTCAAATAGTTTCATGTT
CCCCAAATGGCCCAAAACTGACAGTTTAAACGCTGTCTTGGAACCTAATATGACA
AAAGCGTGATCTCATCCAAGATGAACTAAGTTTGGTTCGTTGAAATGCTAACGGC
CAGTTGGTCAAAAAGAAACTTCCAAAAGTCGGCATACCGTTTGTCTTGTTTGGTA
TTGATTGACGAATGCTCAAAAATAATCTCATTAATGCTTAGCGCAGTCTCTCTAT
CGCTTCTGAACCCCGGTGCACCTGTGCCGAAACGCAAATGGGGAAACACCCGCT
TTTTGGATGATTATGCATTGTCTCCACATTGTATGCTTCCAAGATTCTGGTGGGAA
TACTGCTGATAGCCTAACGTTCATGATCAAAATTTAACTGTTCTAACCCCTACTTG
ACAGCAATATATAAACAGAAGGAAGCTGCCCTGTCTTAAACCTTTTTTTTTATCA
TCATTATTAGCTTACTTTCATAATTGCGACTGGTTCCAATTGACAAGCTTTTGATT
TTAACGACTTTTAACGACAACTTGAGAAGATCAAAAAACAACTAATTATTCGAA
ACG

FIG. 3

GENOMIC SEQUENCE, 1000BP UPSTREAM OF AOX1 PROMOTER ATG
(SEQ ID NO: 4)

CATGTTGGTATTGTGAAATAGACGCAGATCGGGAACACTGAAAAATAACAGTTA
TTATTCGAGATCTAACATCCAAAGACGAAAGGTTGAATGAAACCTTTTTGCCATC
CGACATCCACAGGTCCATTCTCACACATAAGTGCCAAACGCAACAGGAGGGGAT
ACACTAGCAGCAGACCGTTGCAAACGCAGGACCTCCACTCCTCTTCTCCTCAACA
CCCACTTTTGCCATCGAAAAACCAGCCCAGTTATTGGGCTTGATTGGAGCTCGCT
CATTCCAATTCCTTCTATTAGGCTACTAACACCATGACTTTATTAGCCTGTCTATC
CTGGCCCCCCTGGCGAGGTTCATGTTTGTTTATTTCCGAATGCAACAAGCTCCGC
ATTACACCCGAACATCACTCCAGATGAGGGCTTTCTGAGTGTGGGGTCAAATAGT
TTCATGTTCCCCAAATGGCCCAAAACTGACAGTTTAAACGCTGTCTTGGAACCTA
ATATGACAAAAGCGTGATCTCATCCAAGATGAACTAAGTTTGGTTCGTTGAAATG
CTAACGGCCAGTTGGTCAAAAAGAAACTTCCAAAAGTCGGCATACCGTTTGTCTT
GTTTGGTATTGATTGACGAATGCTCAAAAATAATCTCATTAATGCTTAGCGCAGT
CTCTCTATCGCTTCTGAACCCCGGTGCACCTGTGCCGAAACGCAAATGGGGAAAC
ACCCGCTTTTTGGATGATTATGCATTGTCTCCACATTGTATGCTTCCAAGATTCTG
GTGGGAATACTGCTGATAGCCTAACGTTCATGATCAAAATTTAACTGTTCTAACC
CCTACTTGACAGCAATATATAAACAGAAGGAAGCTGCCCTGTCTTAAACCTTTTT
TTTTATCATCATTATTAGCTTACTTTCATAATTGCGACTGGTTCCAATTGACAAGC
TTTTGATTTTAACGACTTTTAACGACAACTTGAGAAGATCAAAAAACAACTAATT
ATTCGAAACG

FIG. 4

| Promoter | SEQ ID NO: | Forward primer | Primer sequence | Primer position on the Promoter sequence |
|---|---|---|---|---|
| Chr1-0469 | 5 | 095F-long | ATCCCTACACGCTCAGGCTT | -570 |
| Upp | 6 | 014-F778 | NNNGGTCTCNATCCTCGCTGGGTGAAAGCCAAC | -778 |
| Upp | 7 | 014-F513 | NNNGGTCTCNATCCGCAGATACGTTCAGTGGTTTCC | -513 |
| Upp | 8 | 014-F354 | NNNGGTCTCNATCCAGTACCTGTGACCGCAATTC | -354 |
| Upp | 9 | 014-F4 | NNNGGTCTCNA<u>TCCTGCCTCAGGTGCATAACTT</u> | -221 |
| GAP | 10 | GAP-F1 | NNNGGTCTCNATCC<u>AATGGACCAAATTGTTGCAAGGT</u> | -619 |
| DAS | 11 | 226F620 | NNNGGTC<u>TCCATCCCTTTGTTGAGCAACA</u> | -382 |
| DAS | 12 | 226F518 | NNNGGTCTCGATCCGCCCAAACGAACAG | -483 |
| AOX | 13 | AOXF1 | NNNGGTCTCCATCCAAAGACGAAAGGTTGAATGA | -931 |

FIG. 8

Alpha-X-Gal plate assay for alpha-Galactosidase activity of *Pichia pastoris* transformants harboring a construct of a synthetic reporter alpha-gal ORF fused with an isolated promoter sequences (SEQ ID NO:). No promoter has been inserted into a control plasmid.
All constructs are integrated into genome of the transformants.

| Position | 1 | 2 | 3 | 4 | 5 |
|---|---|---|---|---|---|
| Row | | | Plate A | | |
| A | | XXX | XXX | XXX | |
| B | XXX | XXX | XXX | XXX | XXX |
| C | Control | XXX | XXX | XXX | XXX |
| D | XXX | XXX | XXX | XXX | XXX |
| E | Control | Control | XXX | XXX | XXX |
| F | XXX | XXX | XXX | XXX | NO:2(-513) |
| G | NO:2 (-354) | DAS | NO:1 (-570) | GAP | |
| H | XXX | XXX | XXX | XXX | XXX |
| I | XXX | XXX | XXX | XXX | |
| J | | XXX | XXX | | |

| Position | 1 | 2 | 3 | 4 | 5 |
|---|---|---|---|---|---|
| Row | | | Plate B | | |
| A | XXX | XXX | XXX | XXX | |
| B | XXX | XXX | XXX | XXX | XXX |
| C | XXX | XXX | XXX | XXX | XXX |
| D | XXX | XXX | XXX | XXX | XXX |
| E | XXX | XXX | XXX | XXX | XXX |
| F | NO:2 (-513) | NO:2 (-354) | DAS | NO:1 (-570) | GAP |
| G | XXX | NO:2 (-221) | XXX | XXX | |
| H | XXX | XXX | XXX | XXX | |
| I | | XXX | XXX | XXX | |
| J | | | XXX | | |

panel A
FIGURE 9A panel B panel C

Phytase activity (plate assay). Pichia pastoris transformants harboring isolated promoter constructs regulating the yeast are pro alpha mazing factor fused, in frame with the Eco 1 appAZ phytase, integrated into genome of the host Pichia cells. The cultures were spotted on the surface of diagnostic plates containing calcium phytate (glucose, upper panel, and methanol, lower panel) and incubated for 27 hours.

| A | B | C | D | E |
|---|---|---|---|---|
| GAP | No. 1 | No. 2 | No. 2 | No. 2 |

Glucose

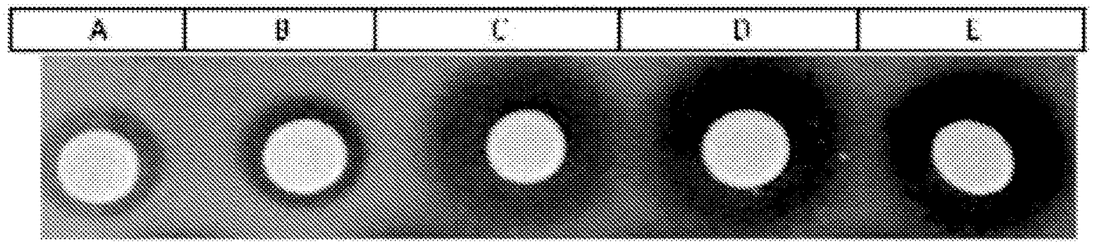

Methanol

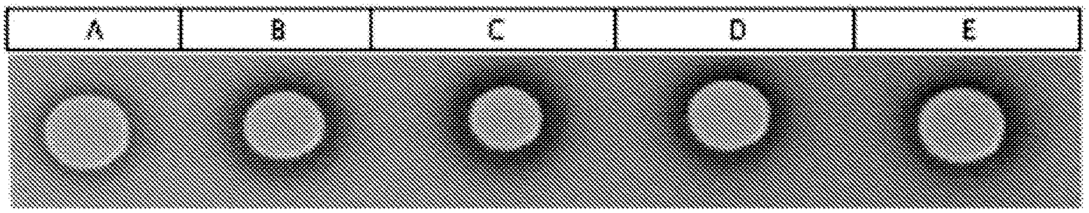

FIG. 10

YEAST PROMOTERS FROM *PICHIA PASTORIS*

CROSS-REFERENCE TO RELATED APPLICATIONS

This application is a U.S. national application filed under 37 C.F.R. § 371(b) of International Application Serial No. PCT/US2014/022135, filed Mar. 7, 2014, which claims the benefit of U.S. Provisional App. Ser. No. 61/774,982 filed Mar. 8, 2013, both of which are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 10, 2015, is named 62472-242094_SL.txt and is 8,640 bytes in size.

FIELD OF THE DISCLOSURE

The present invention is related to isolated nucleic acids, expression methods, host cells, expression vectors, and DNA constructs for producing proteins, and to the proteins produced using the expression methods. More particularly, the invention relates to nucleic acids isolated from *Pichia pastoris* wherein the nucleic acids have promoter activity. The invention also relates to expression methods, host cells, expression vectors, and DNA constructs, for using the *Pichia pastoris* promoters to produce proteins, and to the proteins produced using the expression methods.

BACKGROUND AND SUMMARY OF THE INVENTION

Yeast expression systems can be used to effectively produce proteins, such as enzymes, hormones, and vaccine proteins, in part, because some yeast grow rapidly to high cell densities, are grown in simple and inexpensive media, and are eukaryotes so they can modify proteins in a manner similar to native proteins in mammals. Additionally, with a proper signal sequence, the expressed protein can be secreted into the culture medium for convenient isolation and purification. Some yeast expression systems are also accepted in the food and pharmaceutical industries as being safe for the production of pharmaceuticals and food products, unlike fungal and bacterial expression systems which may in some cases be unsafe, for example, for human food manufacturing.

Thus, it is beneficial for a variety of industries, such as the food and animal feed industries, the human and animal health industries, and the like, to develop or improve yeast expression systems that can be used to express high levels of proteins to increase yield, reduce the expense of isolation and purification of proteins, and reduce the costs of human and animal health products and food products.

A variety of types of yeast expression systems have been developed involving either the use of inducible or constitutive expression of proteins using nucleic acids encoding homologous or heterologous proteins, under the control of a yeast promoter. Promoters are regulatory elements that are linked to the 5' end of a nucleic acid encoding a protein, and may interact with various regulatory factors in the host cell (e.g., a yeast host cell) to control transcription of RNA from DNA. Promoters may also control the timing of transcription of RNA from DNA. For example, the AOX 1 promoter has been identified in the yeast *Pichia pastoris*, and is commonly used in yeast expression systems because it is a tightly regulated, strong promoter.

Due to the importance of yeast expression systems for a variety of industries, including the human pharmaceuticals industry, and the human food and animal feed industries, the improvement of yeast expression systems is the focus of much research and development. Accordingly, the present inventors have identified promoters from *Pichia pastoris* that are particularly effective for use in expression of proteins in yeast. The promoters described herein can be used, for example, in systems for the constitutive expression of proteins.

In one illustrative embodiment of the invention, an isolated nucleic acid is provided wherein the sequence of the isolated nucleic acid comprises a sequence, for example, at least 90%, 95%, or 98% identical to a sequence selected from the group consisting of SEQ ID NO:1 and SEQ ID NO:2 as described herein, or at least 90%, 95%, or 98% identical to a fragment thereof, wherein the isolated nucleic acid comprises the sequence of a constitutive *Pichia pastoris* promoter. In other embodiments, expression vectors, host cells, and DNA constructs comprising these promoter sequences are provided.

In another embodiment, a method of producing a protein using these promoter sequences is provided. The method comprises the steps of culturing in a culture medium a host cell comprising a first expression cassette comprising any of the above promoter sequences operably linked to a heterologous coding sequence encoding a protein, wherein the culturing is done under conditions permitting expression of the protein. In another illustrative embodiment, an isolated protein produced according to this method is provided.

All of the embodiments described in the following clause list are also contemplated for use in accordance with the invention. For all of the embodiments described in the following clauses, any applicable combination of embodiments is considered to be in accordance with the invention.

1. An isolated nucleic acid wherein the sequence of the isolated nucleic acid comprises a sequence at least 90% identical to a sequence selected from the group consisting of SEQ ID NO:1 and SEQ ID NO:2, or at least 90% identical to a fragment thereof, wherein the isolated nucleic acid comprises the sequence of a constitutive *Pichia pastoris* promoter.

2. The isolated nucleic acid of clause 1 wherein the sequence of the isolated nucleic acid is at least 95% identical to a sequence selected from the group consisting of SEQ ID NO:1 and SEQ ID NO:2, or at least 95% identical to a fragment thereof.

3. The isolated nucleic acid of clause 1 wherein the sequence of the isolated nucleic acid is at least 98% identical to a sequence selected from the group consisting of SEQ ID NO:1 and SEQ ID NO:2, or at least 98% identical to a fragment thereof.

4. The isolated nucleic acid sequence of clause 1 wherein the sequence of the isolated nucleic acid is a sequence selected from the group consisting of SEQ ID NO:1 and SEQ ID NO:2, or a fragment thereof.

5. The isolated nucleic acid of any one of clauses 1 to 4 operably linked to a heterologous coding sequence.

6. The isolated nucleic acid of clause 5 wherein the heterologous coding sequence encodes a protein selected from the group consisting of a toxin, an antibody, a hormone, an enzyme, a growth factor, a cytokine, a structural protein, an immunogenic protein, and a cell signaling protein.

7. The isolated nucleic acid of clause 6 wherein the protein is an enzyme for use in animal feed.

8. The isolated nucleic acid of clause 7 wherein the protein is selected from the group consisting of a phytase, a mannanase, a galactosidase, an amylase, a glucanase, a protease, a cellulase, and a xylanase.

9. The isolated nucleic acid of clause 8 wherein the protein is a phytase.

10. The isolated nucleic acid of clause 8 wherein the protein is a galactosidase.

11. An expression vector comprising the isolated nucleic acid of any one of clauses 1 to 10.

12. A host cell comprising the expression vector of clause 11.

13. A host cell comprising the isolated nucleic acid of any one of clauses 1 to 10.

14. The host cell of any one of clauses 12 or 13 wherein the host cell is a *Pichia* species.

15. The host cell of clause 14 wherein the *Pichia* species is *Pichia pastoris.*

16. A DNA construct comprising the isolated nucleic acid of any one of clauses 1 to 10.

17. A method of producing a protein, the method comprising the step of culturing in a culture medium a host cell comprising a first expression cassette comprising the isolated nucleic acid of any one of clauses 1 to 4 operably linked to a heterologous coding sequence encoding a protein, wherein the culturing is done under conditions permitting expression of the protein.

18. The method of clause 17 wherein the protein is selected from the group consisting of a toxin, an antibody, a hormone, an enzyme, a growth factor, a cytokine, a structural protein, an immunogenic protein, and a cell signaling protein.

19. The method of clause 18 wherein the protein is an enzyme for use in animal feed.

20. The method of clause 19 wherein the protein is selected from the group consisting of a phytase, a mannanase, a galactosidase, an amylase, a glucanase, a cellulase, a protease, and a xylanase.

21. The method of clause 20 wherein the protein is a phytase.

22. The method of clause 20 wherein the protein is a galactosidase.

23. The method of any one of clauses 17 to 22 wherein the protein is expressed using the first expression cassette in combination with a second expression cassette.

24. The method of clause 23 wherein the second expression cassette comprises the heterologous coding sequence encoding the protein operably linked to an isolated nucleic acid having a sequence comprising the sequence of SEQ ID NO:3 or SEQ ID NO:4 wherein SEQ ID NO:3 and SEQ ID NO:4 have promoter activity, or any other AOX 1 or AOX 2 promoter sequence.

25. The method of clause 24 wherein the protein is expressed using the first expression cassette, the second expression cassette, and a third expression cassette.

26. The method of clause 25 wherein the third expression cassette comprises the heterologous coding sequence encoding the protein operably linked to an isolated nucleic acid having a sequence at least 90% identical to a sequence selected from the group consisting of SEQ ID NO:1 and SEQ ID NO:2, or at least 90% identical to a fragment thereof.

27. The method of clause 23 wherein the second expression cassette comprises the heterologous coding sequence encoding the protein operably linked to an isolated nucleic acid having a sequence at least 90% identical to a sequence selected from the group consisting of SEQ ID NO:1 and SEQ ID NO:2, or at least 90% identical to a fragment thereof.

28. An isolated protein produced according to the method of any one of clauses 17 to 27.

29. The host cell of any one of clauses 12 or 13 wherein the host cell is a methylotrophic yeast.

30. The host cell of clause 29 wherein the host cell is selected from the group consisting of *Hansenula* species, *Pichia* species, and *Candida* species.

31. A host cell comprising the DNA construct of clause 16 wherein the host cell is a methylotrophic yeast.

32. The host cell of clause 31 selected from the group consisting of *Hansenula* species, *Pichia* species, and *Candida* species.

33. The method of any one of clauses 17 to 27 wherein the host cell is a methylotrophic yeast.

34. The method of clause 33 wherein the host cell is selected from the group consisting of *Hansenula* species, *Pichia* species, and *Candida* species.

35. The method of clause 25 wherein the third expression cassette comprises the heterologous coding sequence encoding the protein operably linked to an isolated nucleic acid having a sequence of SEQ ID NO:3 or SEQ ID NO:4 wherein SEQ ID NO:3 and SEQ ID NO:4 have promoter activity, or any other AOX 1 or AOX2 promoter sequence.

36. A method of producing one or more proteins, the method comprising the step of culturing in a culture medium a host cell comprising a first expression cassette, a second expression cassette, and one or more additional expression cassettes, wherein each of the one or more additional expression cassettes comprises the isolated nucleic acid of any one of clauses 1 to 4 operably linked to a heterologous coding sequence encoding the one or more proteins, wherein the culturing is done under conditions permitting expression of the one or more proteins.

37. The method of clause 17 further comprising the step of purifying the protein from the medium of the cultured host cell.

38. The method of clause 36 further comprising the step of purifying one or more of the one or more proteins from the medium of the cultured host cell.

39. The isolated nucleic acid, host cell, expression vector, isolated protein, DNA construct, or method of any one of clauses 1 to 38 wherein the isolated nucleic acid consists of any one of SEQ ID NOS. 1 to 2, or a fragment thereof.

40. An isolated nucleic acid consisting of any one of SEQ ID NOS. 1 to 2, or a fragment thereof.

41. The host cell of clause 12 or 13 wherein the host cell is selected from the group consisting of *Hansenula* species, *Pichia* species, *Saccharomyces* species, *Schizosaccharomyces* species, *Torulaspora* species, a *Candida* species, a *Yarrowia* species, and *Kluveromyces* species.

42. The isolated nucleic acid of clause 5 wherein the heterologous coding sequence encodes a protein or polypeptide selected from the group consisting of a toxin, an antibody, a hormone, an enzyme, a growth factor, a cytokine, a structural protein, an immunogenic protein, and a cell signaling protein.

43. A method of producing a protein or a polypeptide, the method comprising the step of culturing in a culture medium a host cell comprising a first expression cassette comprising the isolated nucleic acid of any one of clauses 1 to 4 operably linked to a heterologous coding sequence encoding a protein, wherein the culturing is done under conditions permitting expression of the protein.

44. The method of clause 23 wherein the second expression cassette comprises the heterologous coding sequence encoding the protein operably linked to an isolated nucleic acid having a sequence comprising the sequence of SEQ ID NO:3 or SEQ ID NO:4 wherein SEQ ID NO:3 and SEQ ID NO:4 have promoter activity, or any other promoter sequence.

45. The method of clause 25 wherein the third expression cassette comprises the heterologous coding sequence encoding the protein operably linked to an isolated nucleic acid having a sequence of SEQ ID NO:3 or SEQ ID NO:4 wherein SEQ ID NO:3 and SEQ ID NO:4 have promoter activity, or any other promoter sequence.

BRIEF DESCRIPTION OF THE DRAWINGS

FIG. 1 shows the nucleotide sequence of the Chr1-0469 promoter (SEQ ID NO: 1).

FIG. 2 shows the nucleotide sequence of the UPP promoter (SEQ ID NO: 2).

FIG. 3 shows the nucleotide sequence of the AOX1 promoter sequence (SEQ ID NO:3).

FIG. 4 shows the genomic sequence 1000 bp upstream of the AOX1 promoter ATG start codon (SEQ ID NO:4).

FIG. 8 shows the nucleotide sequence of forward primers (SEQ ID NOS: 5-13, respectively, in order of appearance) used for isolation of the Chr1-0469 promoter (SEQ ID NO: 1) and the UPP promoter (SEQ ID NO: 2) from *Pichia pastoris* genomic DNA by PCR. The corresponding DNA fragments—products of these PCR reactions—are introduced into the reporter vector with the alpha-Galactosidase ORF (FIG. 7).

FIG. 10 shows the activity of the *E. coli* appA2 phytase in *Pichia pastoris.*

DETAILED DESCRIPTION OF THE ILLUSTRATIVE EMBODIMENTS

Figure 5:
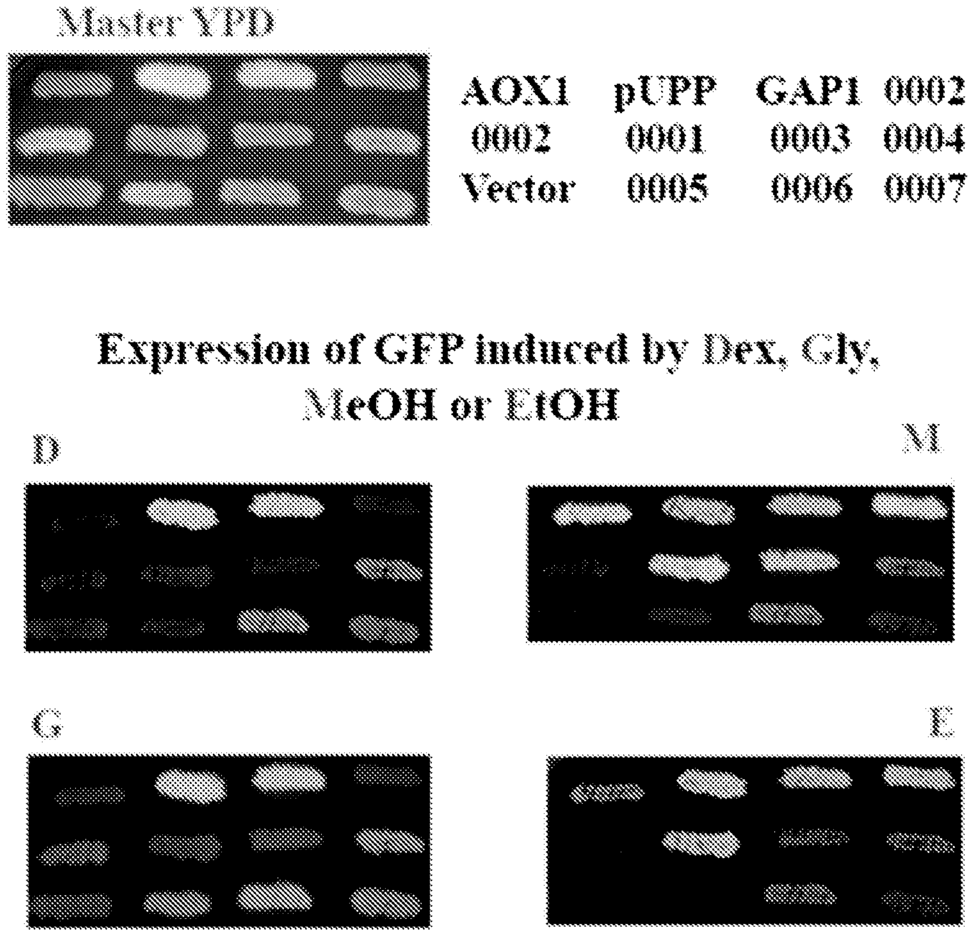
FIG. 5 shows the level of GFP expression for various transformants in replica plates.

In one illustrative embodiment of the invention, an isolated nucleic acid is provided wherein the sequence of the isolated nucleic acid comprises a sequence, for example, at least 90%, 95%, or 98% identical to a sequence selected from the group consisting of SEQ ID NO:1 and SEQ ID NO:2 as described herein, or at least 90%, 95%, or 98% identical to a fragment thereof, wherein the nucleic acid comprises the sequence of a constitutive *Pichia pastoris* promoter. In another embodiment, the isolated nucleic acid sequence is a sequence selected from the group consisting of SEQ ID NO:1 and SEQ ID NO:2, or a fragment thereof. In other embodiments, expression vectors, host cells, and DNA constructs comprising these promoter sequences are provided.

The above-described promoters have been isolated from a yeast strain (i.e., NRRL Y11430) currently classified as a *Pichia pastoris* yeast strain. However, the classification may change at some point to a *Komagataella* species (e.g., *Komagataella phaffii*).

In another embodiment, a method of producing a protein using these promoter sequences is provided. The method comprises the steps of culturing in a culture medium a host cell comprising a first expression cassette comprising any of the above promoter sequences operably linked to a heterologous coding sequence encoding a protein, wherein the culturing is done under conditions permitting expression of the protein. In another illustrative embodiment, an isolated protein produced according to this method is provided.

All of the embodiments described in the following clause list are contemplated for use in accordance with the invention. For all of the embodiments described in the following clauses, any applicable combination of embodiments is considered to be in accordance with the invention. Any embodiment described in the following clause list is also contemplated for use with any embodiment described in the Summary of Invention section of this application or in the Detailed Description of the Illustrative Embodiments section of this application.

1. An isolated nucleic acid wherein the sequence of the isolated nucleic acid comprises a sequence at least 90% identical to a sequence selected from the group consisting of SEQ ID NO:1 and SEQ ID NO:2, or at least 90% identical to a fragment thereof, wherein the isolated nucleic acid comprises the sequence of a constitutive *Pichia pastoris* promoter.

2. The isolated nucleic acid of clause 1 wherein the sequence of the isolated nucleic acid is at least 95% identical to a sequence selected from the group consisting of SEQ ID NO:1 and SEQ ID NO:2, or at least 95% identical to a fragment thereof.

3. The isolated nucleic acid of clause 1 wherein the sequence of the isolated nucleic acid is at least 98% identical to a sequence selected from the group consisting of SEQ ID NO:1 and SEQ ID NO:2, or at least 98% identical to a fragment thereof.

4. The isolated nucleic acid sequence of clause 1 wherein the sequence of the isolated nucleic acid is a sequence selected from the group consisting of SEQ ID NO:1 and SEQ ID NO:2, or a fragment thereof.

5. The isolated nucleic acid of any one of clauses 1 to 4 operably linked to a heterologous coding sequence.

6. The isolated nucleic acid of clause 5 wherein the heterologous coding sequence encodes a protein selected from the group consisting of a toxin, an antibody, a hormone, an enzyme, a growth factor, a cytokine, a structural protein, an immunogenic protein, and a cell signaling protein.

7. The isolated nucleic acid of clause 6 wherein the protein is an enzyme for use in animal feed.

8. The isolated nucleic acid of clause 7 wherein the protein is selected from the group consisting of a phytase, a mannanase, a galactosidase, an amylase, a glucanase, a protease, a cellulase, and a xylanase.

9. The isolated nucleic acid of clause 8 wherein the protein is a phytase.

10. The isolated nucleic acid of clause 8 wherein the protein is a galactosidase.

11. An expression vector comprising the isolated nucleic acid of any one of clauses 1 to 10.

12. A host cell comprising the expression vector of clause 11.

13. A host cell comprising the isolated nucleic acid of any one of clauses 1 to 10.

14. The host cell of any one of clauses 12 or 13 wherein the host cell is a *Pichia* species.

15. The host cell of clause 14 wherein the *Pichia* species is *Pichia pastoris.*

16. A DNA construct comprising the isolated nucleic acid of any one of clauses 1 to 10.

17. A method of producing a protein, the method comprising the step of culturing in a culture medium a host cell comprising a first expression cassette comprising the isolated nucleic acid of any one of clauses 1 to 4 operably linked to a heterologous coding sequence encoding a protein, wherein the culturing is done under conditions permitting expression of the protein.

18. The method of clause 17 wherein the protein is selected from the group consisting of a toxin, an antibody, a hormone, an enzyme, a growth factor, a cytokine, a structural protein, an immunogenic protein, and a cell signaling protein.

19. The method of clause 18 wherein the protein is an enzyme for use in animal feed.

20. The method of clause 19 wherein the protein is selected from the group consisting of a phytase, a mannanase, a galactosidase, an amylase, a glucanase, a cellulase, a protease, and a xylanase.

21. The method of clause 20 wherein the protein is a phytase.

22. The method of clause 20 wherein the protein is a galactosidase.

23. The method of any one of clauses 17 to 22 wherein the protein is expressed using the first expression cassette in combination with a second expression cassette.

24. The method of clause 23 wherein the second expression cassette comprises the heterologous coding sequence encoding the protein operably linked to an isolated nucleic acid having a sequence comprising the sequence of SEQ ID NO:3 or SEQ ID NO:4 wherein SEQ ID NO:3 and SEQ ID NO:4 have promoter activity, or any other AOX 1 or AOX 2 promoter sequence.

25. The method of clause 24 wherein the protein is expressed using the first expression cassette, the second expression cassette, and a third expression cassette.

26. The method of clause 25 wherein the third expression cassette comprises the heterologous coding sequence encoding the protein operably linked to an isolated nucleic acid having a sequence at least 90% identical to a sequence selected from the group consisting of SEQ ID NO:1 and SEQ ID NO:2, or at least 90% identical to a fragment thereof.

27. The method of clause 23 wherein the second expression cassette comprises the heterologous coding sequence encoding the protein operably linked to an isolated nucleic acid having a sequence at least 90% identical to a sequence selected from the group consisting of SEQ ID NO:1 and SEQ ID NO:2, or at least 90% identical to a fragment thereof.

28. An isolated protein produced according to the method of any one of clauses 17 to 27.

29. The host cell of any one of clauses 12 or 13 wherein the host cell is a methylotrophic yeast.

30. The host cell of clause 29 wherein the host cell is selected from the group consisting of *Hansenula* species, *Pichia* species, and *Candida* species.

31. A host cell comprising the DNA construct of clause 16 wherein the host cell is a methylotrophic yeast.

32. The host cell of clause 31 selected from the group consisting of *Hansenula* species, *Pichia* species, and *Candida* species.

33. The method of any one of clauses 17 to 27 wherein the host cell is a methylotrophic yeast.

34. The method of clause 33 wherein the host cell is selected from the group consisting of *Hansenula* species, *Pichia* species, and *Candida* species.

35. The method of clause 25 wherein the third expression cassette comprises the heterologous coding sequence encoding the protein operably linked to an isolated nucleic acid having a sequence of SEQ ID NO:3 or SEQ ID NO:4 wherein SEQ ID NO:3 and SEQ ID NO:4 have promoter activity, or any other AOX 1 or AOX 2 promoter sequence.

36. A method of producing one or more proteins, the method comprising the step of culturing in a culture medium a host cell comprising a first expression cassette, a second expression cassette, and one or more additional expression cassettes, wherein each of the one or more additional expression cassettes comprises the isolated nucleic acid of any one of clauses 1 to 4 operably linked to a heterologous coding sequence encoding the one or more proteins, wherein the culturing is done under conditions permitting expression of the one or more proteins.

37. The method of clause 17 further comprising the step of purifying the protein from the medium of the cultured host cell.

38. The method of clause 36 further comprising the step of purifying one or more of the one or more proteins from the medium of the cultured host cell.

39. The isolated nucleic acid, host cell, expression vector, isolated protein, DNA construct, or method of any one of clauses 1 to 38 wherein the isolated nucleic acid consists of any one of SEQ ID NOS. 1 to 2, or a fragment thereof.

40. An isolated nucleic acid consisting of any one of SEQ ID NOS. 1 to 2, or a fragment thereof.

41. The host cell of clause 12 or 13 wherein the host cell is selected from the group consisting of *Hansenula* species, *Pichia* species, *Saccharomyces* species, *Schizosaccharomyces* species, *Torulaspora* species, a *Candida* species, a *Yarrowia* species, and *Kluveromyces* species.

42. The isolated nucleic acid of clause 5 wherein the heterologous coding sequence encodes a protein or polypeptide selected from the group consisting of a toxin, an antibody, a hormone, an enzyme, a growth factor, a cytokine, a structural protein, an immunogenic protein, and a cell signaling protein.

43. A method of producing a protein or a polypeptide, the method comprising the step of culturing in a culture medium a host cell comprising a first expression cassette comprising the isolated nucleic acid of any one of clauses 1 to 4 operably linked to a heterologous coding sequence encoding a protein, wherein the culturing is done under conditions permitting expression of the protein.

44. The method of clause 23 wherein the second expression cassette comprises the heterologous coding sequence encoding the protein operably linked to an isolated nucleic acid having a sequence comprising the sequence of SEQ ID NO:3 or SEQ ID NO:4 wherein SEQ ID NO:3 and SEQ ID NO:4 have promoter activity, or any other promoter sequence.

45. The method of clause 25 wherein the third expression cassette comprises the heterologous coding sequence encoding the protein operably linked to an isolated nucleic acid having a sequence of SEQ ID NO:3 or SEQ ID NO:4 wherein SEQ ID NO:3 and SEQ ID NO:4 have promoter activity, or any other promoter sequence.

The phrase "consists of" or "consisting of" means that the sequence specified by the SEQ ID NO. has no additional nucleotide sequences other than those corresponding to the SEQ ID NO.

Any yeast expression system known to those skilled in the art can be used in accordance with the present invention. For example, various yeast expression systems are described in U.S. Pat. Nos. 6,451,572, 6,841,370, 6,974,690, 7,320,876, 7,078,035, 7,138,260, and PCT Publication No. WO 2007/112739, all incorporated herein by reference. In any of the embodiments described herein, any of these yeast expression systems can be used. Alternatively, any yeast species or yeast expression system suitable for expression of a protein can be used including yeast species, such as *Saccharomyces* species (e.g., *Saccharomyces cerevisiae*), *Kluyveromyces* species (e.g., *Kluyveromyces lactis*), *Torulaspora* species, *Yarrowia* species (e.g., *Yarrowia lipolitica*), *Schizosaccharomyces* species (e.g., *Schizosaccharomyces pombe*). In another embodiment, methylotrophic yeast species such as *Pichia* species (e.g., *Pichia pastoris* or *Pichia methanolica*), *Hansenula* species (e.g., *Hansenula polymorpha*), *Torulopsis* species, *Komagataella* species, *Candida* species (e.g., *Candida boidinii*), and *Karwinskia* species can be used. In one embodiment the protein can be expressed in the methylotrophic yeast *Pichia pastoris*. Methylotrophic yeast are capable of utilizing methanol as a sole carbon source for the production of the energy resources necessary to maintain cellular function. Methylotrophic yeast contain genes encoding enzymes for methanol utilization such as the genes encoding alcohol oxidase. Any of these host cells can be a host cell strain that is heterologous to the promoter described herein (i.e., the host cell does not normally contain in nature the promoter described herein).

A yeast expression system can be used to produce a sufficient amount of the protein intracellularly, or secreted from the yeast cells so that the protein can be conveniently isolated and purified from the culture medium. As used herein, the term "expression" means transcription and/or translation of a nucleic acid in a host cell. A yeast expression system may include, but is not limited to, the yeast host cell and the expression vector (e.g., a DNA construct) used to express the protein. The expression vector can contain a promoter described herein and, as is known in the art, the promoter is heterologous to the expression vector (i.e., the combination does not occur in nature). In one embodiment, secretion of the protein into the culture medium is controlled by a signal peptide (e.g., the yeast $\alpha$-factor signal peptide, the yeast KILM1 signal peptide, the yeast PHO1 signal peptide, or the yeast SUC2 signal peptide) incorporated into the expression vector and which is capable of directing the secretion of the expressed protein out of the yeast cell. In other embodiments, other signal peptides suitable for facilitating secretion of the protein from yeast cells are known to those skilled in the art. In one aspect, the signal peptide is typically cleaved from the protein after secretion.

In various embodiments, any expression vector known to the skilled artisan (e.g., a vector that replicates autonomously or integrates into the host genome) and compatible with a yeast expression system can be used. As used herein, the term "vector" means any plasmid, or other vector, in double-stranded or single-stranded form or in linear or circular form that can transform a yeast cell by integration into the yeast cell genome or by existing extrachromosomally (e.g., an autonomously replicating plasmid). As is known in the art, a vector (e.g., expression vector or expression cassette) is a nucleic acid construct used to transform a host cell for expression of a protein, polypeptide, or peptide and the vector is not found in nature in the host cell it transforms.

In one embodiment, the expression vector has restriction endonuclease cleavage sites for the insertion of DNA fragments (e.g., one or more cloning sites and/or a multiple cloning site), and genetic markers for selection of transformants. For example, the genetic markers for selection of transformants can include a selection marker that allows a transformed yeast to grow on a medium devoid of a necessary nutrient that cannot be produced by a deficient strain, a selection marker that encodes an enzyme for which chromogenic substrates are known, or a selection marker that provides resistance to a drug, including, but not limited to, G418, Nourseothricin (Nat), Zeocin, Blasticidin, or Hygromycin. In another embodiment, the expression vector has a terminator sequence for transcription termination (e.g., the AOX 1 or HSP150 terminator). In another embodiment, the expression vector has a 3' untranslated region downstream from the protein coding sequence with a polyadenylation site. As used herein, "3' untranslated region" means nucleotide sequences that are not translated into protein and are located downstream from a coding sequence for a protein. Typically, a 3' untranslated region includes regulatory sequences for mRNA processing. In another embodiment, the expression vector has an origin of replication (e.g., a bacterial origin of replication) for use in synthesizing and amplifying the vector, for example, in a bacterial host. Various expression vectors are described in U.S. Pat. Nos. 6,451,572, 6,841,370, 6,974,690, 7,320,876, 7,078,035, 7,138,260, and PCT Publication No. WO 2007/112739, all incorporated herein by reference. The construction and use of expression vectors is described in Sambrook et al., "Molecular Cloning: A Laboratory Manual", 3rd Edition, Cold Spring Harbor Laboratory Press, (2001), incorporated herein by reference. In another embodiment, the expression vector, or a fragment thereof, can be synthesized de novo or PCR can be used to amplify and join sections of expression vectors.

As used herein, "regulatory sequences" means nucleotide sequences that are typically upstream or downstream from the 5' or 3' end, respectively, of a protein coding sequence. Regulatory sequences are not translated into protein. Regulatory sequences include, but are not limited to, sequences that affect RNA processing or stability, such as polyadenylation signal sequences, enhancers, repressor binding sites, and promoters.

In one embodiment, the protein coding sequence can be operably linked in the expression vector to the promoter sequence capable of directing the expression of the protein, for example, in yeast. As used herein, "operably linked" means functionally linked. As described herein, the promoter can be a "constitutive promoter". A "constitutive promoter" means a promoter that regulates expression of a gene of interest. The term "constitutive promoter" is known in the art. A constitutive promoter can have some inducible activity, but the maximal activity obtained with the promoter is not inducible.

As used herein "promoter" means a nucleotide sequence typically located upstream from the 5' end of a coding sequence for a protein that controls the transcription of RNA from DNA, in part, by interacting with various regulatory factors that control transcription. In one embodiment, the promoter may be derived from the same species of yeast as the yeast host cell used for protein expression. In another embodiment, the promoter may be derived from a different yeast species than the yeast host cell used for protein expression. In one embodiment, a promoter may include a TATA box sequence that acts as a recognition site to direct initiation of transcription, including, but not limited to one or more transcriptional enhancer elements. The enhancer elements may be proximal or distal to the TATA box sequence and may be in a normal 5' to 3' orientation or may be in a 3' to 5' orientation. In another embodiment, an enhancer element may be an enhancer element native to the promoter sequence or it may be a heterologous enhancer element inserted into the expression vector construct. An “enhancer element” as used herein is a regulatory element that can stimulate promoter activity.

In various illustrative embodiments described herein, the promoter can be an isolated nucleic acid wherein the sequence of the isolated nucleic acid comprises a sequence at least 80%, at least 85%, at least 90%, at least 92%, at least 95%, at least 96%, at least 97%, at least 98%, or at least 99% identical to a sequence selected from the group consisting of SEQ ID NO:1 and SEQ ID NO:2, or at least 80%, at least 85%, at least 90%, at least 92%, at least 95%, at least 96%, at least 97%, at least 98%, or at least 99% identical to a fragment thereof, wherein the isolated nucleic acid comprises the sequence of a constitutive *Pichia pastoris* promoter. In another embodiment, the isolated nucleic acid sequence is a sequence selected from the group consisting of SEQ ID NO:1 and SEQ ID NO:2, or a fragment thereof wherein the isolated nucleic acid comprises the sequence of a constitutive *Pichia pastoris* promoter.

As used herein “an isolated nucleic acid” means a nucleic acid that is substantially free of sequences that naturally flank the nucleic acid in the genomic DNA of the organism from which the nucleic acid is derived. For example, in various embodiments, an isolated nucleic acid in accordance with the invention can contain less than about 2 kb, less than about 1 kb, less than about 0.5 kb, less than about 0.1 kb of nucleotide sequences, less than about 0.05 kb, or no nucleotide sequences that naturally flank the nucleic acid molecule in genomic DNA of the organism from which the isolated nucleic acid is derived.

As used herein, “a fragment thereof” when referring to the isolated nucleic acid molecule means a fragment of the isolated nucleic acid of SEQ ID NOS: 1 to 2. In various illustrative embodiments, the fragment can be about 50 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, or about 900 nucleotides in length. In other embodiments, the fragment can extend about 50 nucleotides, about 100 nucleotides, about 200 nucleotides, about 300 nucleotides, about 400 nucleotides, about 500 nucleotides, about 600 nucleotides, about 700 nucleotides, about 800 nucleotides, or about 900 nucleotides upstream from the 3' end of the isolated nucleic acid of any of SEQ ID NOS: 1 to 2. In yet other embodiments, the fragment can include about 50 nucleotides, about 100 nucleotides, about 200 nucleotides, about 300 nucleotides, or about 350 nucleotides upstream and/or downstream from the TATA box sequence found in each of SEQ ID NOS: 1 to 2.

In various embodiments, the isolated nucleic acids described herein may be purified by techniques for purification of nucleic acids (e.g., DNA) that are well-known in the art. For example, the nucleic acids may be separated from contaminants by physical methods including, but not limited to, centrifugation, pressure techniques, or by using a substance with affinity for nucleic acids (e.g., DNA), such as, for example, silica beads. After sufficient washing, the isolated nucleic acids may be suspended in either water or a buffer. In other embodiments, commercial kits are available, such as Qiagen™, Nuclisensm™, and Wizard™ (Promega), and Promegam™. Methods for purifying nucleic acids are described in Sambrook et al., “Molecular Cloning: A Laboratory Manual”, 3rd Edition, Cold Spring Harbor Laboratory Press, (2001), incorporated herein by reference. An isolated nucleic acid as described herein may be an isolated nucleic acid that is also purified, or the isolated nucleic acid may be impure. A “purified nucleic acid” is substantially free of other cellular material, or culture medium when produced by recombinant techniques, or substantially free of chemical precursors or other chemicals when chemically synthesized.

The isolated nucleic acids described herein are capable of specific hybridization, under appropriate hybridization conditions (e.g., appropriate buffer, ionic strength, temperature, formamide, and $MgCl_2$ concentrations), to a complementary nucleic acid. The isolated nucleic acids described herein can be modified by substitution, deletion, truncation, and/or can be fused with other nucleic acid molecules wherein the resulting isolated nucleic acids hybridize specifically to the complementary nucleic acids.

Also within the scope of the invention are nucleic acids complementary to the isolated nucleic acids, or fragments thereof, described herein, and those that hybridize to the isolated nucleic acids described herein or those that hybridize to their complements under highly stringent conditions. As used herein, the term “complementary” refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have “complementary” sequences. The complementary DNA sequences are referred to as a “complement.”

In accordance with the invention “highly stringent conditions” means hybridization at 65° C. in 5×SSPE and 50% formamide, and washing at 65° C. in 0.5×SSPE. Conditions for high stringency hybridization are described in Sambrook et al., “Molecular Cloning: A Laboratory Manual”, 3rd Edition, Cold Spring Harbor Laboratory Press, (2001), incorporated herein by reference. In some illustrative aspects, hybridization can occur along the full-length of the isolated nucleic acid, or along part of its length, or to a fragment thereof.

Also included are isolated nucleic acid molecules having about 60%, about 70%, about 75%, about 80%, about 85%, about 90%, about 92%, about 95%, 96%, 97%, 98%, and 99% identity to the isolated nucleic acids described herein, or to a fragment thereof. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the isolated nucleic acid sequence of interest, or the sequence of a fragment thereof. Algorithms for database searching are typically based on the BLAST software (Altschul et al., 1990). In some embodiments, the percent identity can be determined along the full-length of the isolated nucleic acid.

Techniques for synthesizing the isolated nucleic acids described herein are well-known in the art and include chemical syntheses and recombinant methods. Such techniques are described in Sambrook et al., "Molecular Cloning: A Laboratory Manual", 3rd Edition, Cold Spring Harbor Laboratory Press, (2001), incorporated herein by reference. Isolated nucleic acid molecules can also be made commercially. Techniques for synthesizing the isolated nucleic acids described herein are well-known in the art. The isolated nucleic acids described herein can be analyzed by techniques known in the art, such as restriction enzyme analysis or sequencing, to determine the sequence of the isolated nucleic acids. Thus, isolated nucleic acids described herein may be synthetic.

In illustrative aspects, yeast cells are transformed with an expression vector comprising a heterologous nucleic acid encoding the protein of interest operably linked to one of the promoters described herein using procedures well-known to those skilled in the art. The term "transformation" means the transfer of a nucleic acid, or a nucleic acid fragment, into a host cell. In illustrative embodiments, such transformation protocols include electroporation, lithium acetate methods, and use of spheroplasts. In illustrative aspects, the expressed nucleic acid coding sequence can be a heterologous nucleic acid coding sequence. As used herein, a heterologous coding sequence is defined as an artificial or synthetic nucleic acid or a nucleic acid originating from a different species than the species from which the promoter sequence was derived. Thus, a heterologous coding sequence linked to a promoter described herein does not occur in nature.

In various embodiments, the transformed yeast cells may be grown by techniques including batch and continuous fermentation in a liquid medium or on a semi-solid medium, or a solid medium. Typically, "conditions permitting expression of the protein" as used herein means conditions for batch or continuous fermentation of yeast in a liquid medium, but growth on a semi-solid medium, such as agar, is not excluded. Culture media for yeast cells are known in the art and are typically supplemented with a carbon source (e.g., glucose). A typical yeast culture medium is YPD broth (Sunrise Science Products, Inc.) comprising yeast extract (10 grams), Bacto peptone (20 grams), and dextrose (20 grams). In one illustrative aspect, the transformed yeast cells can be grown aerobically at 30° C. in a controlled pH environment (a pH of about 6) and with the carbon source (e.g., glucose) maintained continuously at a predetermined level known to support growth of the yeast cells to a desired density within a specific period of time.

In one illustrative embodiment, a method of producing a protein is provided. The method comprises the step of culturing in a culture medium a host cell comprising a first expression cassette comprising an isolated nucleic acid of any one of SEQ ID NOS: 1 to 2, or a fragment thereof, operably linked to a heterologous coding sequence encoding a protein, wherein the culturing is done under conditions permitting expression of the protein. The method can further comprise the step of purifying the protein from the medium of the cultured host cell. As used herein, an "expression cassette" means the elements of an expression vector that direct the yeast cell to make RNA. An expression cassette comprises at least regulatory sequences (e.g., a promoter) and a coding sequence for the RNA and protein (i.e., an open reading frame, ORF). The isolated nucleic acid can be at least 80%, at least 85%, at least 90%, 92%, 95%, 96%, 97%, 98%, or 99% homologous to the isolated nucleic acid of any of SEQ ID NOS: 1 to 2, or a fragment thereof. In various illustrative aspects, the protein coding sequence can be from a bacterium, a yeast, a fungus, or a virus.

In this method embodiment, the protein can be expressed using the first expression cassette in combination with a second expression cassette. In another embodiment, the second expression cassette can comprise 1) the heterologous coding sequence encoding the protein operably linked to an isolated nucleic acid having a sequence comprising the sequence of SEQ ID NO:3 or SEQ ID NO:4 wherein SEQ ID NO:3 and SEQ ID NO:4 have promoter activity, or any other known methanol-regulated promoter, such as AOX 1, AOX 2, FLD, or DAS promoter sequences, or 2) the isolated nucleic acid of any one of SEQ ID NOS: 1 to 2, or a fragment thereof, operably linked to the heterologous coding sequence encoding the protein.

In yet another embodiment, the protein can be expressed using the first expression cassette, the second expression cassette, and a third expression cassette. In another illustrative aspect, the third expression cassette can comprise 1) the heterologous coding sequence encoding the protein operably linked to an isolated nucleic acid having a sequence comprising the sequence of SEQ ID NO:3 or SEQ ID NO:4 wherein SEQ ID NO:3 and SEQ ID NO:4 have promoter activity, or any other known methanol-regulated promoters, such as AOX 1, AOX 2, FLD, or DAS promoter sequences, or 2) the isolated nucleic acid of any one of SEQ ID NOS: 1 to 2, or a fragment thereof, operably linked to the heterologous coding sequence encoding the protein.

In another embodiment, any number of additional expression cassettes can be used and the expression cassettes can comprise 1) the heterologous coding sequence encoding the protein operably linked to an isolated nucleic acid having a sequence comprising the sequence of SEQ ID NO:3 or SEQ ID NO:4 wherein SEQ ID NO:3 and SEQ ID NO:4 have promoter activity, or any other known methanol-regulated promoters, such as AOX 1, AOX 2, FLD, or DAS promoter sequences, or 2) the isolated nucleic acid of any one of SEQ ID NOS: 1 to 2, or a fragment thereof, operably linked to the heterologous coding sequence encoding the protein. In another embodiment, the first expression cassette, the second expression cassette, and the third expression cassette as described above are used in the method, along with a fourth expression cassette, a fifth expression cassette, and a sixth expression cassette wherein all of the expression cassettes comprise the isolated nucleic acid of any one of SEQ ID NOS: 1 to 2, or a fragment thereof, operably linked to the heterologous coding sequence encoding the protein.

In still another embodiment, a method of producing one or more proteins is provided. The method comprises the step of culturing in a culture medium a host cell comprising a first expression cassette, a second expression cassette, and, optionally, one or more additional expression cassettes, wherein each of the expression cassettes comprises 1) a heterologous coding sequence encoding the one or more proteins operably linked to an isolated nucleic acid having a sequence comprising the sequence of SEQ ID NO:3 or SEQ ID NO:4 wherein SEQ ID NO:3 and SEQ ID NO:4 have promoter activity, or any other known methanol-regulated promoters, such as AOX 1, AOX 2, FLD, or DAS promoter sequences, or 2) the isolated nucleic acid of any one of SEQ ID NOS: 1 to 2, or a fragment thereof, operably linked to a heterologous coding sequence encoding the one or more proteins, wherein the culturing is done under conditions permitting expression of the one or more proteins. The method can further comprise the step of purifying one of the one or more proteins from the medium of the cultured host cell.

In any of the embodiments described in the preceding two paragraphs, the isolated nucleic acid can be at least 80%, at least 85%, at least 90%, 92%, 95%, 96%, 97%, 98%, or 99% homologous to the isolated nucleic acid of any of SEQ ID NOS: 1 to 2, or a fragment thereof. In any of the embodiments described in the preceding two paragraphs, the expression cassettes can be included in one expression vector or in multiple expression vectors. In any of the embodiments described in the preceding two paragraphs, the expression vectors into which the expression cassettes are incorporated can be vectors that replicate autonomously or that integrate into the host cell genome.

In various illustrative embodiments, the protein encoded by the any of the heterologous coding sequences described herein operably linked to the promoter can be a protein selected from the group consisting of a toxin, an antibody, a hormone, an enzyme, a growth factor, a cytokine, a structural protein, an immunogenic protein (e.g., a vaccine antigen), and a cell signaling protein. In one embodiment, the protein is an enzyme for use in animal feed. In this embodiment, the protein can be selected from the group consisting of a phytase, a mannanase, a galactosidase, an amylase, a glucanase, a cellulase, a protease, and a xylanase. In another embodiment, the protein can be an enzyme useful for glycosylation. In another aspect, more than one protein can be expressed by using multiple expression cassettes, each with a heterologous coding sequence, operably linked to a promoter. However, these protein examples are non-limiting and any protein or peptide or polypeptide capable of being expressed in yeast can be expressed in accordance with the isolated nucleic acids, expression vectors, host cells, DNA constructs, methods, and isolated proteins described herein. The enzymes described above can be from any species (e.g., fungal species, such as a yeast species).

The yeast-expressed proteins for use in accordance with the present invention can be produced in purified form by conventional techniques. As used herein, "isolated protein" means a purified protein. A purified protein is substantially free from other yeast cell contaminants or contaminants from the culture medium. For example, "substantially free" from other yeast cell contaminants or contaminants from the culture medium means that the protein is at least about 60% pure, at least about 70% pure, at least about 80% pure, at least about 90% pure, at least about 95% pure, at least about 98% pure, about 60% pure, about 70% pure, about 80% pure, about 90% pure, about 95% pure, or about 98% pure (all based on dry weight). Typically, the protein is secreted into the yeast culture medium and is collected from the culture medium.

In one illustrative embodiment, for purification from the culture medium the protein can, for example, be subjected to ammonium sulfate precipitation followed by DEAE-Sepharose column chromatography. In other embodiments, conventional techniques known to those skilled in the art can be used such as ammonium sulfate or ethanol precipitation, acid extraction, gel filtration, anion or cation exchange chromatography, DEAE-Sepharose column chromatography, hydroxylapatite chromatography, lectin chromatography, affinity chromatography, solvent-solvent extraction, ultrafiltration, and HPLC.

Alternatively, purification steps may not be required because the protein may be present in such high concentrations in the culture medium that the protein is essentially pure in the culture medium (e.g., 70 to 80% pure). In one embodiment, the protein is collected from the culture medium without further purification steps by chilling the yeast culture (e.g., to about 4° C. to about 8° C.) and removing the yeast cells using such techniques as centrifugation, microfiltration, and rotary vacuum filtration. The protein in the cell-free medium can then be concentrated by such techniques as, for example, ultrafiltration and tangential flow filtration.

In some embodiments where the protein is not secreted into the culture medium, the yeast cells can be lysed, for example, by sonication, heat, or chemical treatment, and the homogenate centrifuged to remove cell debris. The supernatant can then be subjected to ammonium sulfate precipitation, and additional fractionation techniques as required, such as gel filtration, ion exchange chromatography, DEAE-Sepharose column chromatography, affinity chromatography, solvent-solvent extraction, ultrafiltration, and HPLC to purify the protein. It should be understood that the purification methods described above for purification of proteins from the culture medium or from lysed yeast cells are non-limiting and any purification techniques known to those skilled in the art can be used to purify the yeast-expressed protein if such techniques are required to obtain a substantially pure protein.

Various formulations of the purified protein preparations may be prepared in accordance with the invention. In some embodiments, the proteins can be stabilized through the addition of other proteins (e.g., gelatin and skim milk powder), chemical agents (e.g., glycerol, polyethylene glycol, EDTA, potassium sorbate, sodium benzoate, and reducing agents and aldehydes), polysaccharides, monosaccharides, lipids (hydrogenated vegetable oils), and the like. In one embodiment, proteins for addition to food products or animal feed blends can be dried (e.g., spray drying, drum drying, and lyophilization) and formulated as powders, granules, pills, mineral blocks, liquids, and gels through known processes. In one embodiment, gelling agents such as gelatin, alginate, collagen, agar, pectin and carrageenan can be used.

In alternate embodiments, the protein expression can be for intracellular expression, such as for enzymatic action in the yeast in a biotransformation process, or for display on the yeast cell surface. For such embodiments, the protein, expressed as described herein, is not purified.

In various embodiments, the proteins described above are selected from the group consisting of a toxin, an antibody, a hormone, an enzyme, a growth factor, a cytokine, a structural protein, an immunogenic protein (e.g., a vaccine antigen), and a cell signaling protein. In another embodiment, the proteins described above are selected from the group consisting of an antibody, a hormone, an enzyme, a growth factor, a cytokine, a structural protein, an immunogenic protein (e.g., a vaccine antigen), and a cell signaling protein. In yet another embodiment the coding sequence for a protein, a fragment thereof, a fusion protein (e.g., a chimeric protein), or a peptide, can be used in accordance with the invention. In another embodiment, a modified protein can be expressed, such as a mutated protein or a protein with non-natural amino acids.

In one embodiment, the toxins can be proteins such as, for example, botulinum toxin or verotoxin-1, and after preparation using the methods, isolated nucleic acids, expression vectors, host cells, and DNA constructs described herein, the toxins can be modified using a targeting agent so that they are directed specifically to diseased cells. In another illustrative aspect, the antibody can be a humanized antibody, an antibody that is not humanized, a nanobody, or an antibody fragment, such as an Fab fragment of an antibody or a single-chain antibody. In another embodiment, the hormone can be, for example, a gonadotropin, an adrenocorticotrophic hormone, a growth hormone, vasopressin, oxytocin, somatostatin, gastrin, or leptin. In another illustrative embodiment, the growth factor can be insulin, epidermal growth factor, fibroblast growth factor, vascular endothelial growth factor, erythropoietin, platelet-derived growth factor, thrombopoietin, or a bone morphogenic protein. In one aspect, the cytokine can be IL-2, IFN-α, IFN-γ, or GM-CSF. In one embodiment, the protein is not a silk toxin. In another illustrative aspect, the vaccine proteins can be any suitable vaccine proteins that are immunogenic in a patient or an animal, including, but not limited to, HPV proteins (e.g., HPV 16 and HPV 18), and tetanus vaccine proteins, as examples. In another illustrative embodiment, the enzymes can be, for example, enzymes for animal feeds as discussed herein, acetylcholinesterase, or cyclooxygenase, or any other useful enzyme that can be expressed in yeast. In another embodiment, structural proteins can be expressed, for example, netrins, actin-binding proteins, or myosin, and, in another embodiment, cell signaling proteins such as ras proteins, kinases, the ErbB2 protein (the Her-2 receptor) can be expressed using the methods, isolated nucleic acids, expression vectors, host cells, and DNA constructs described herein.

In one embodiment, the protein is an enzyme for use in animal feed. In this embodiment, the protein can be selected from the group consisting of a phytase, a mannanase, a galactosidase, an amylase, a glucanase, a cellulase, a protease, and a xylanase, or a combination thereof. For example, a variety of phytases may be expressed according to the methods described herein. Exemplary of phytase genes (i.e., a phytase coding sequence) that can be expressed in accordance with the invention are phytase genes derived from bacteria, filamentous fungi, plants, and yeast, such as the appA (Gene Bank accession number M58708) and appA2 (Gene Bank accession number 250016) genes derived from *Escherichia coli* and the phyA and phyB genes derived from the fungus *Aspergillus niger*, or any mutant of these genes that retains or has improved myo-inositol hexakisphosphate phosphohydrolase activity (see, for example, Rodriguez et al., *Arch. of Biochem. and Biophys.* 382: 105-112 (2000), incorporated herein by reference). Exemplary alpha- and beta-galactosidase genes are from *Aspergillus* species (e.g., *Aspergillus alliaceus, Aspergillus orzae, Aspergillus nidulans, Aspergillus parasiticus*, and *Aspergillus niger*). Substituted, deleted, and truncated phytase genes, or a fragment thereof, can also be expressed in accordance with the invention.

In one embodiment, the protein expressed using the methods described herein can be used in animal feed comprising an animal feed blend. In various embodiments, any animal feed blend known in the art can be used such as rapeseed meal, cottonseed meal, soybean meal, and cornmeal. Optional ingredients of the animal feed blend include sugars and complex carbohydrates such as both water-soluble and water-insoluble monosaccharides, disaccharides and polysaccharides. Optional amino acid ingredients that can be added to the feed blend are arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that can be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. Minerals, protein ingredients, including protein obtained from meat meal or fish meal, liquid or powdered egg, fish solubles, whey protein concentrate, oils (e.g., soybean oil), cornstarch, calcium, inorganic phosphate, copper sulfate, salt, and limestone can also be added. Antioxidants can also be added.

In another embodiment, a kit comprising an expression vector comprising the isolated nucleic acid of SEQ ID NO: 1 to SEQ ID NO: 2, or a fragment thereof, is provided. In one illustrative aspect, the isolated nucleic acid, or the fragment, can be 80%, 85%, 90%, 92%, 95%, 96%, 97%, 98%, or 99% identical to the isolated nucleic acid of SEQ ID NO: 1 to SEQ ID NO: 2, or to the fragment thereof. In various illustrative embodiments, the fragment can be about 50 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, or about 900 nucleotides in length. In other embodiments, the fragment can extend about 50 nucleotides, about 100 nucleotides, about 200 nucleotides, about 300 nucleotides, about 400 nucleotides, about 500 nucleotides, about 600 nucleotides, about 700 nucleotides, about 800 nucleotides, or about 900 nucleotides upstream from the 3' end of the isolated nucleic acid of any of SEQ ID NOS: 1 to 2. In yet other embodiments, the fragment can include about 50 nucleotides, about 100 nucleotides, about 200 nucleotides, about 300 nucleotides, or about 350 nucleotides upstream and/or downstream from the TATA box sequence found in each of SEQ ID NOS: 1 to 2.

In one embodiment, the expression vector (i.e., with the heterologous promoter) included in the kit can have any of the other elements described herein, such as a selection marker, a cloning site, such as a multiple cloning site, an enhancer, a termination sequence, a signal peptide sequence, and the like. In another aspect, the expression vector can be a vector that replicates autonomously or integrates into the host cell genome. In another embodiment, the expression vector can be circularized or linearized (i.e., digested with a restriction enzyme so that a gene of interest can easily be cloned into the expression vector). In another embodiment, the kit can include an expression vector and a control ORF encoding a marker or control gene for expression (e.g., an ORF encoding a LacZ-α fragment) for use as a control to show that the expression vector is competent to be ligated and to be used with a gene of interest.

In another illustrative embodiment, the kit can contain a tube containing a circular expression plasmid. In another embodiment, the kit can contain a tube with a linear expression vector that is digested with a restriction enzyme so it is ready to clone a gene of interest. In one embodiment, the tube can be sterilized. In either of these embodiments, the kit can also include a circular or linear expression vector and a control ORF encoding a marker or control gene for expression (e.g., an ORF encoding a LacZ-α fragment) for use as a control in showing that the expression vector can be ligated with a gene of interest, and/or to show that the host cell is competent for transformation.

In yet another embodiment, the kit can contain multiple different expression vectors. In another embodiment, the multiple different expression vectors can contain the same promoter, but different selectable markers, such as genes for resistance to the drugs G418, Nourseothricin (Nat), Zeocin, Blasticidin, or Hygromycin. In this embodiment, the kit may also contain aliquots of the drugs (e.g., G418, Nourseothricin (Nat), Zeocin, Blasticidin, or Hygromycin) in tubes, or other containers, separate from the corresponding vectors.

In any of the kit embodiments described above, the isolated nucleic acid can consist of any one of SEQ ID NOS. 1 to 2, or a fragment thereof. The phrase "consists of" means that the sequence specified by the SEQ ID NO. has no additional nucleotide sequences other than those corresponding to the SEQ ID NO.

In another illustrative aspect, the kit can include other components for use with the expression vector, such as components for transformation of yeast cells, restriction enzymes for incorporating a protein coding sequence of interest into the expression vector, ligases, components for purification of expression vector constructs, buffers (e.g., a ligation buffer), instructions for use (e.g., to facilitate cloning), and any other components suitable for use in a kit for making and using the expression vectors described herein. In another embodiment, the expression vector or any other component of the kit can be included in the kit in a sealed tube (e.g., sterilized or not sterilized) or any other suitable container or package (e.g., sterilized or not sterilized). The kits described in the preceding paragraphs that include the expression vector comprise the expression vector comprising a promoter described herein operably linked to the vector which is heterologous to the promoter (i.e., the combination does not occur in nature).

The following examples provide illustrative methods for carrying out the practice of the present invention. As such, these examples are provided for illustrative purposes only and are not intended to be limiting.

EXAMPLES

Example 1: Preparation of Promoter Sequences and Promoter-Containing Plasmids Microarray "chips" to measure *Pichia pastoris* mRNA levels were created by Affymetrix (Affymetrix, Inc.) using *Pichia* genomic DNA sequence provided by Dr. James Cregg. Microarray chips were probed with RNA samples from yeast cultures grown on different carbon sources, including methanol, glycerol and ethanol. Cultures were harvested at various time points in mid-log phase and frozen for the subsequent RNA isolation as recommended by Affymetrix. Standard Affymetrix protocols for probing Affymetrix microarrays were followed.

Total RNA from each cell sample was extracted by a glass bead breakage/phenol extraction/LiCl precipitation method. RNA was converted to cDNA and subsequently amplified and labeled to probe Affymetrix chips. Labeled cDNAs were hybridized to Affymetrix *Pichia pastoris* microarray chips and evaluated using Affymetrix software. Data analysis identified genes induced by methanol (relative to glycerol) or genes expressed under most conditions (i.e., constitutively expressed) as shown in Table 1.

Table 1 lists the relative mRNA levels from the indicated genes comparing promoter activity from *Pichia pastoris* cells grown on media with methanol, glycerol or ethanol as the carbon source.

TABLE 1

Relative Activity of Promoters

| | | Relative Promoter Activity | | | |
|---|---|---|---|---|---|
| Protein | Gene | Methanol | MeOH starvation | Glycerol | Ethanol |
| Hypothetical protein | UPP | 9942 | 8297 | 9512 | 10673 |
| Protein Translation Elongation Factor 1A | TEF2 | 8910 | 5626 | 9309 | 9471 |
| Hypothetical protein | Chr1-0469 | 6904 | 192 | 7673 | 7618 |
| Glyceraldehyde 3-phosphate dehydrogenase | GAP | 5685 | 4688 | 6701 | 6069 |
| AOX1 Average | AOX1 | 9127 | 4974 | 610 | 361 |
| Dihydroxy-acetone synthase | DAS | 8533 | 2591 | 1211 | 796 |

Figure 6:
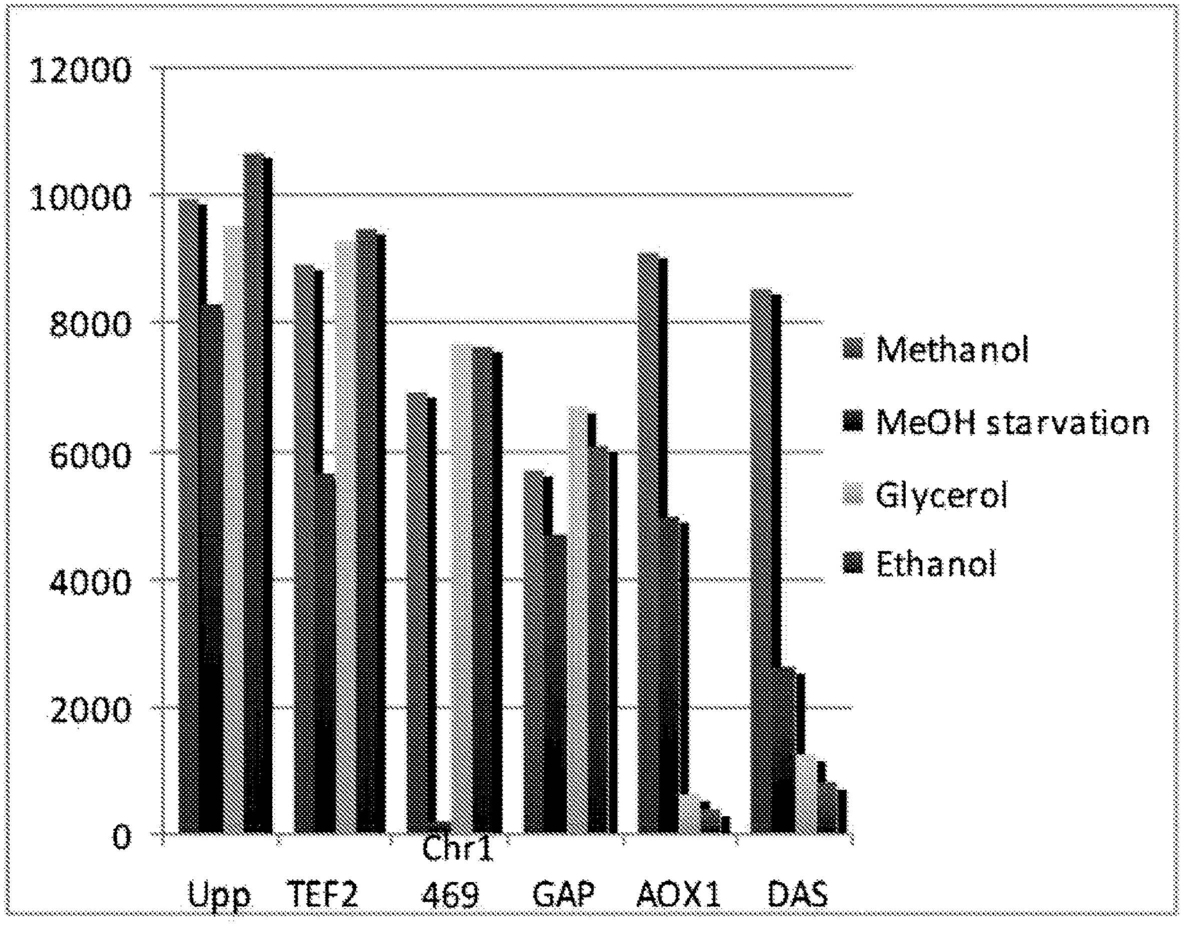
FIG. 6 shows the relative promoter activity for pUPP, TEF2, Chr1-0469, GAP, AOX1, and DAS promoters under various conditions.

FIG. 6 shows the relative promoter activity for pUPP, TEF2, Chr1-0469, GAP, AOX1, and DAS using the carbon sources methanol (leftmost bar in each set of bars), methanol starvation (bar second from the left in each set of bars), glycerol (bar third from the left in each set of bars), and ethanol (rightmost bar in each set of bars). The hypothetical proteins are the ORFs for the UPP and Chr1-0469 promoters.

Promoters from two constitutively expressed genes were cloned and tested with reporter vectors. All of the reporter plasmids were missing promoter elements to drive expression of the reporter ORF; alternatively, a cloning scheme utilizing Type II restriction enzymes (i.e. BsaI) was put in place to introduce DNA fragments (promoters) upstream of the ORF. All constructs contained the same 3'AOX1 transcriptional terminator sequence after the stop codon of the reporter ORF.

One reporter plasmid, pTZ-GFP, is a derivative of pJAZ (zeocin resistance as a selection marker) without the AOX1 promoter, but with a green fluorescent protein (GFP) ORF as a reporter gene for intracellular expression. A second group of reporter plasmids contains selectable marker genes for zeocin or G418 resistance and the *Aspergillus* alpha-galactosidase or beta-galactosidase ORFs as reporters for intracellular expression. The third group of reporter plasmids has the *S. cerevisiae* pre-pro-alpha Mating Factor (aMF) signal for secretion fused in frame with the *E. coli* appA2 coding sequence for phosphatase (phytase), as the reporter ORF. None of the reporter plasmid sequences are expressed in *Pichia pastoris* without the introduction of a sequence that has promoter activity upstream of the reporter ORF.

Two of the most active constitutive promoters, from the UPP and Chr1-0469 genes, consisted of the DNA ~1000 bp "upstream" of ORF's of unknown function. These promoter sequences were amplified using PCR primers and *Pichia pastoris* genomic DNA. The sequence of the PCR products was confirmed, prior to ligation into reporter plasmids. The UPP promoter was cloned using strategically placed BsaI sites in the primers flanking the promoter. The Chr1-0469 promoter contains recognition sites for BsaI and BsmBI; therefore, cloning ends were created by a PCR-denaturation-annealing procedure. Briefly, the promoter was amplified with two sets of primers. The PCR products represent two nearly identical double-stranded DNA molecules except that the ends are off-set by 4 bp (one is four nucleotides shorter from the 5'-end and four nucleotides longer from the 3'-end, and the other four nucleotides longer from the 5'-end and four nucleotides shorter from the 3'-end). The two different PCR products are mixed, denatured and annealed to create promoter molecules with the proper 4 base single strand extensions at each end of the molecule ("sticky" ends to facilitate cloning). Cloning ends, generated by BsaI digestion or by PCR-denaturation-annealing, were complementary to ends created in the reporter plasmids. Promoters regulating the *Pichia pastoris* AOX1 and GAP1 genes were introduced into the same reporter constructs as controls.

The promoter specific plasmid constructs were linearized by digestion with specific restriction enzymes and introduced into wild type *Pichia pastoris* cells by electroporation. Transformants containing the plasmid DNA integrated into the genome of the host strain were selected on YPD agar with either zeocin or G418. Single colonies from the transformation were purified (again on selective plates), then, multiple clones were collected on YPD master plates. These master plates were replica-plated to a series of diagnostic plates with agar media containing one of the following compounds as the only carbon source for growth of the *Pichia pastoris* cells: glucose (i.e., dextrose), glycerol, methanol, or ethanol (all at 1% w/v). Plates were incubated at 30° C. for 20 to 44 hours before scoring.

Example 2: Determination of GFP Expression in Transformants

The relative level of GFP expression between the various transformants was compared. In this example, replica plates were exposed to UV light using a transilluminator and the fluorescence intensity of the different strains was compared by direct visualization. *Pichia* cells without GFP expression, negative colonies, did not demonstrate GFP fluorescence under UV illumination. The intensity of the observed fluorescence correlated with an increase in GFP expression.

FIG. 5 is an example of GFP expression for various transformants on replica plates with different carbon sources. The location of the different *Pichia* promoter strains in each panel is the same, and the "Master YPD" panel identifies the location of the strains by their promoter designation: AOX1, pUPP, GAP1, 0001, 0002, 0003, 0004, 0005, 0006, 0007, and Vector (mock control). The lower part of FIG. 5, labeled as "Expression of GFP induced by Dex, Gly, MeOH, or EtOH" shows that the carbon source used in each panel is dextrose (D), glycerol (G), methanol (M) or ethanol (E), respectively. The data show that the UPP promoter is as strong or stronger than the GAP promoter under the conditions tested, and is stronger than the AOX promoter under most conditions tested.

Figure 7:
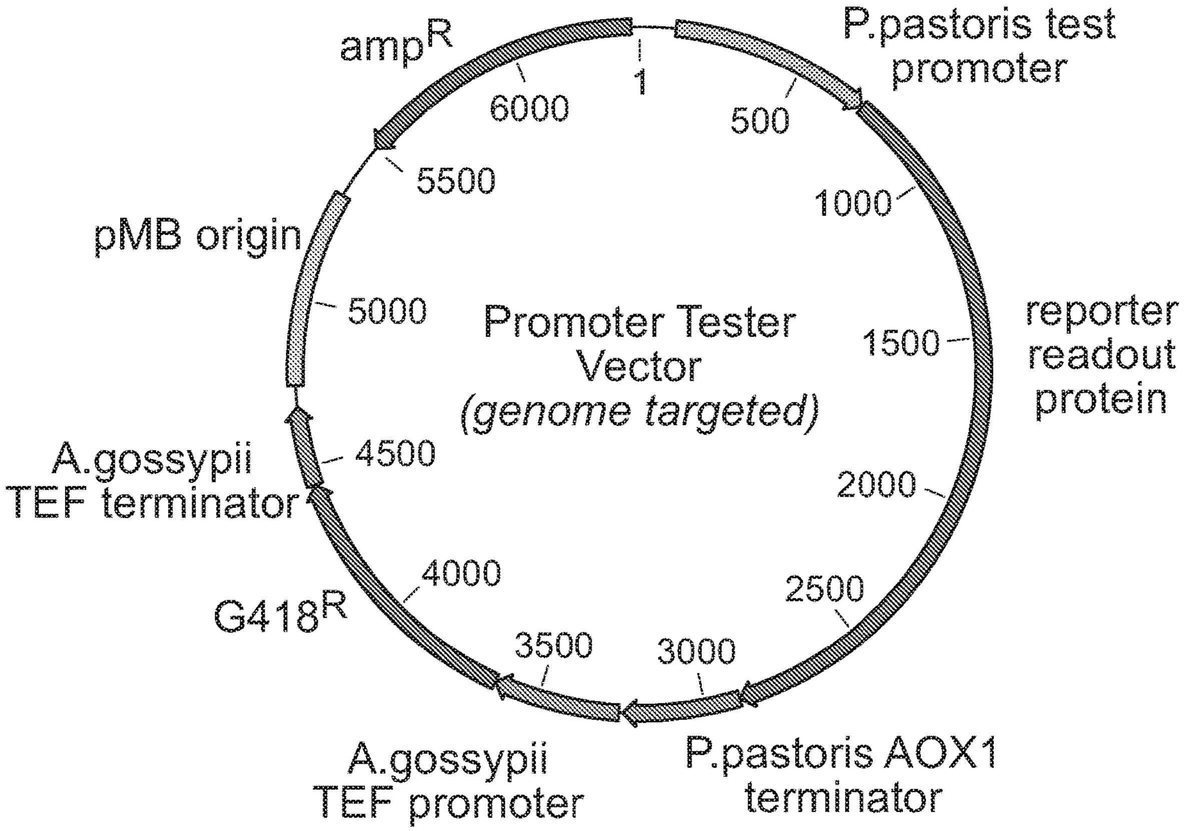
FIG. 7 shows the map of a reporter vector. Similar vectors were used with both the alpha and beta-Galactosidase ORF, as well as with, or without a secretion signal (alpha mating factor)

Example 3: Determination of Relative Activity of Alpha- and Beta-Galactosidases of Transformants The UPP promoter and the Chr1-0469 promoter sequences were amplified using PCR primers and *Pichia pastoris* genomic DNA (the sequences of the forward primers used for amplification of the promoter fragments are shown on FIG. 8). The sequences of the PCR products were confirmed, prior to ligation into the alpha-GAL reporter plasmid (FIG. 7). Promoters regulating the *Pichia pastoris* GAP, TEF2, DAS and AOX1 ORFs were introduced into the same reporter plasmid as controls. The sequences of the inserted promoter fragments were confirmed by sequencing the entire insertions, in both directions, using plasmid specific primers located upstream of the inserted fragment (forward primers) and in the 5' region of the alpha-Galactosidase ORF (reverse primers). The promoter specific plasmid constructs were linearized by digestion with specific restriction enzymes and introduced into wild type *Pichia pastoris* cells by electroporation, and transformants containing the plasmid DNA integrated into the genome of the host strain were selected. Cells from well isolated, single-colony transformants were purified and collected on a YPD master plate and incubated at 30° C. The master plate was subsequently replica-plated to a series of diagnostic plates with agar media containing one of the following compounds as the only carbon source for growth of the *Pichia pastoris* cells: glucose (i.e., dextrose), glycerol, methanol, or ethanol (all at 1% w/v) and alpha-X-Gal chromogenic substrate. These plates were then incubated at 30° C. for 44 hours (FIG. 9).

The expression level from the different promoter-alpha-galactosidase reporter gene constructs, was determined by the observation of the alpha-galactosidase from YPD agar plates made with 100 mM phosphate buffer, pH 6.5, and alpha-X-GAL as a chromogenic substrate. Reporter activity was detected as a blue colored product in, or around the cells. Reporter activity was demonstrated with the UPP and Chr1-0469 promoters.

Figure 9B:
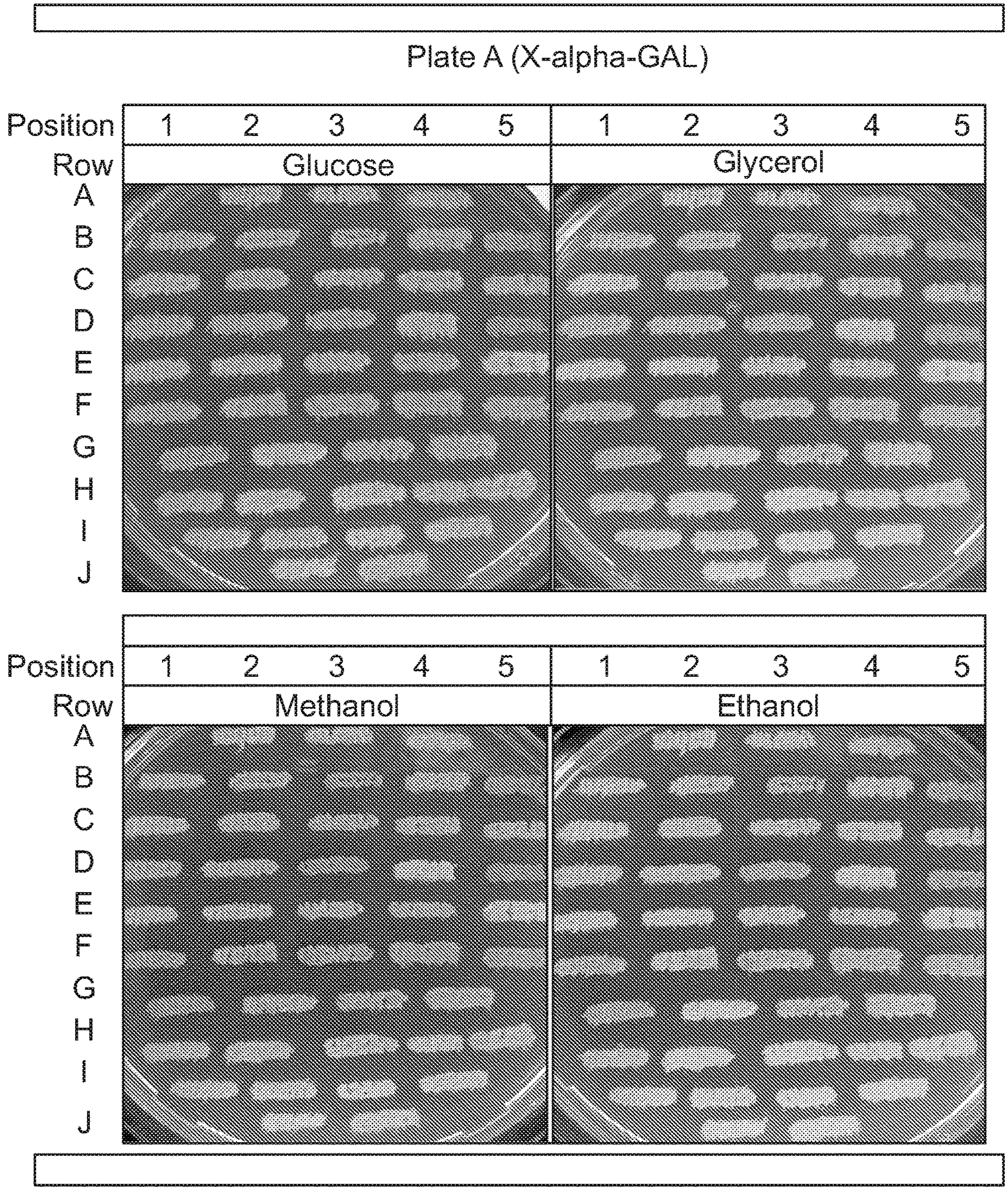
FIG. 9 A-C show the level of alpha-Galactosidase expression from isolated transformants with the indicated promoter-reporter constructs.
Figure 9C:
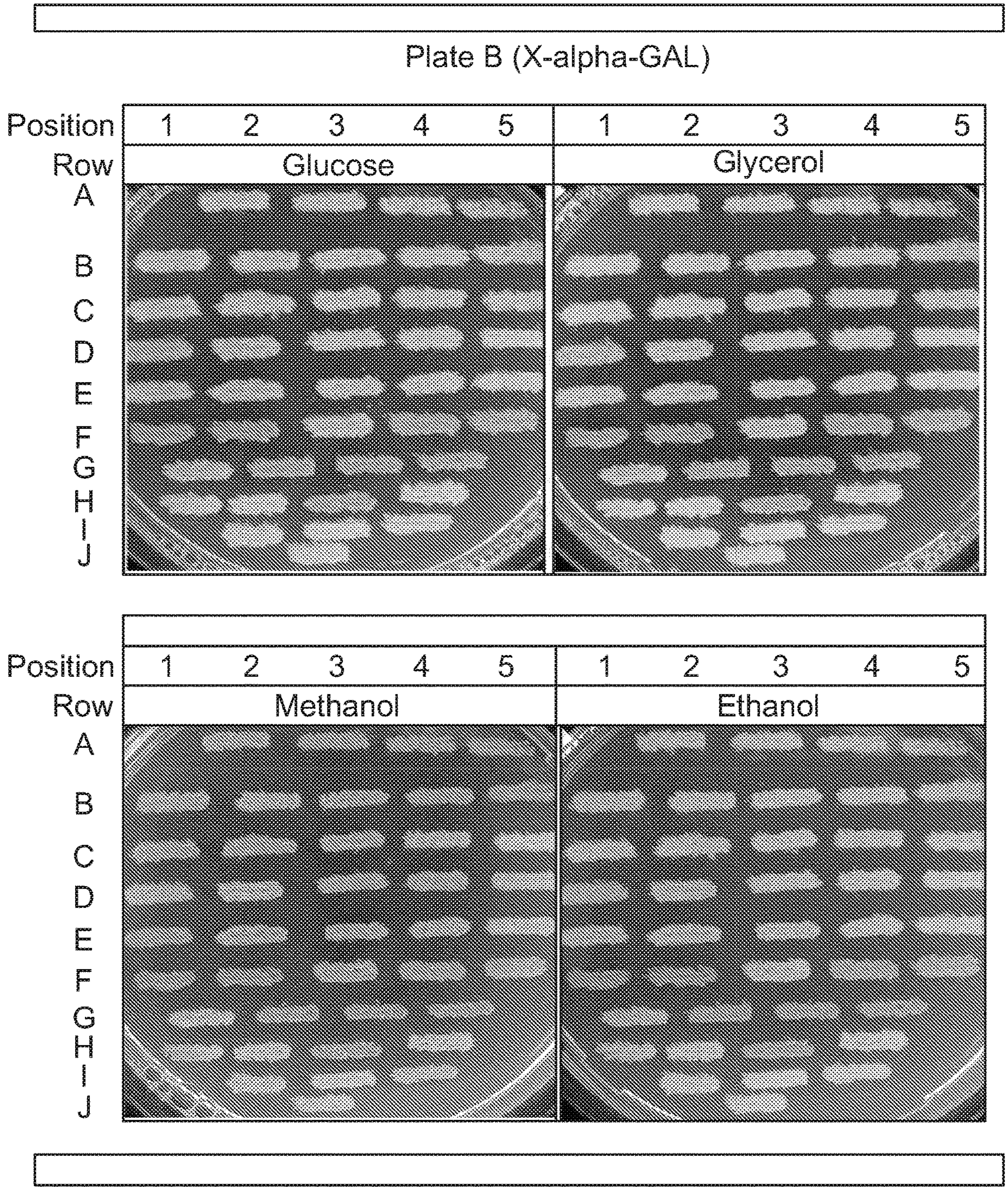

The promoter designations in FIG. 9A-C correspond to the Chr1-0469 promoter (SEQ ID NO: 1) and the UPP promoter (SEQ ID NO: 2). The length of each promoter fragment is indicated with the +1 position equal to the A in the ATG start codon of the corresponding gene in the *Pichia pastoris* genome (therefore the promoter sequences are from −1 to −1500). Fragments of other *Pichia pastoris* promoters as well as a reporter vector without any promoter sequences are used as controls. The transformants were incubated on agar plates containing X-alpha-GAL, a chromogenic substrate for alpha-Galactosidase, and one of four carbon sources as indicated. Plates A and B in FIG. 9A, were replica-plated on different carbon sources to plates A and B, respectively, shown in FIG. 9B and FIG. 9C, respectively. Thus, the designations in FIG. 9A of plates A and B refer to FIG. 9B and FIG. 9C, respectively. The notations of NO:1 and NO:2 refer to SEQ ID NOS: 1 and 2 (i.e., to the promoter used to express α-galactosidase). The level of α-galactosidase expression with the promoters is shown in the tables labeled Plate A and Plate B below on the various carbon sources. The level of α-galactosidase expression is shown as 0, +1, +2, +3, +4, and +5, with the level of expression increasing from 0 to +5.

Similarly, the beta-Galactosidase ORF was used for analysis of expression of the reporter constructs with the Chr1-0469 promoter and the UPP promoter sequences in the *Pichia pastoris* transformants. In these experiments the expression level from the beta-galactosidase reporter gene was determined on plates with beta-X-GAL as a chromogenic substrate. Reporter activity with beta-Galactosidase ORF was also demonstrated with both the UPP and Chr1-0469 promoters.

Relative Alpha-Galactosidase Expression, Plate A, from FIG. 9.

| Promoter (seq ID/name) | FIG. 9 (Panel/ row/ column) | Carbon Source | Relative A-gal expression (1-5) |
|---|---|---|---|
| Control | A/C/1 | Glucose | 0 |
| Control | A/E/1 | Glucose | 0 |
| Control | A/E/2 | Glucose | 0 |
| UPP-513 (No: 2) | A/F/5 | Glucose | 4 |
| UPP-354 (No: 2) | A/G/1 | Glucose | 4 |
| DAS | A/G/2 | Glucose | 0 |
| 1-0469 (No: 1) | A/G/3 | Glucose | 4 |
| GAP | A/G/4 | Glucose | 3 |
| Control | A/C/1 | Glycerol | 0 |

-continued

Relative Alpha-Galactosidase Expression, Plate A, from FIG. 9.

| Promoter (seq ID/name) | FIG. 9 (Panel/ row/ column) | Carbon Source | Relative A-gal expression (1-5) |
|---|---|---|---|
| Control | A/E/1 | Glycerol | 0 |
| Control | A/E/2 | Glycerol | 0 |
| UPP-513 (No: 2) | A/F/5 | Glycerol | 3 |
| UPP-354 (No: 2) | A/G/1 | Glycerol | 4 |
| DAS | A/G/2 | Glycerol | 0 |
| 1-0469 (No: 1) | A/G/3 | Glycerol | 3 |
| GAP | A/G/4 | Glycerol | 2 |
| Control | A/C/1 | Methanol | 1 |
| Control | A/E/1 | Methanol | 0 |
| Control | A/E/2 | Methanol | 1 |
| UPP-513 (No: 2) | A/F/5 | Methanol | 3 |
| UPP-354 (No: 2) | A/G/1 | Methanol | 4 |
| DAS | A/G/2 | Methanol | 2 |
| 1-0469 (No: 1) | A/G/3 | Methanol | 3 |
| GAP | A/G/4 | Methanol | 3 |
| Control | A/C/1 | Ethanol | 0 |
| Control | A/E/1 | Ethanol | 0 |
| Control | A/E/2 | Ethanol | 0 |
| UPP-513 (No: 2) | A/F/5 | Ethanol | 3 |
| UPP-354 (No: 2) | A/G/1 | Ethanol | 4 |
| DAS | A/G/2 | Ethanol | 0 |
| 1-0469 (No: 1) | A/G/3 | Ethanol | 3 |
| GAP | A/G/4 | Ethanol | 2 |

Relative Alpha-Galactosidase Expression, Plate B, from FIG. 9

| Promoter (seq ID/name) | FIG. 9 (Plate B/ row/ column) | Carbon Source | Relative A-gal expression (1-5) |
|---|---|---|---|
| UPP-513 (No: 2) | B/F/1 | Glucose | 4 |
| UPP-345 (No: 2) | B/F/2 | Glucose | 4 |
| DAS | B/F/3 | Glucose | 0 |
| 1-0469 (No: 1) | B/F/4 | Glucose | 3 |
| GAP | B/F/5 | Glucose | 4 |
| UPP-222 (No: 2) | B/G/2 | Glucose | 3 |
| UPP-513 (No: 2) | B/F/1 | Glycerol | 4 |
| UPP-345 (No: 2) | B/F/2 | Glycerol | 4 |
| DAS | B/F/3 | Glycerol | 0 |
| 1-0469 (No: 1) | B/F/4 | Glycerol | 3 |
| GAP | B/F/5 | Glycerol | 4 |
| UPP-222 (No: 2) | B/G/2 | Glycerol | 3 |
| **Promoter (seq ID/name)** | **FIG. 9 (Plate/ row/ column)** | **Carbon Source** | **Relative A-gal expression (1-5)** |
| UPP-513 (No: 2) | B/F/1 | Methanol | 5 |
| UPP-345 (No: 2) | B/F/2 | Methanol | 5 |
| DAS | B/F/3 | Methanol | 3 |
| 1-0469 (No: 1) | B/F/4 | Methanol | 3 |
| GAP | B/F/5 | Methanol | 3 |
| UPP-222 (No: 2) | B/G/2 | Methanol | 4 |

-continued

Relative Alpha-Galactosidase Expression, Plate B, from FIG. 9

| Promoter (seq ID/name) | FIG. 9 (Plate B/ row/ column) | Carbon Source | Relative A-gal expression (1-5) |
|---|---|---|---|
| UPP-513 (No: 2) | B/F/1 | Ethanol | 4 |
| UPP-345 (No: 2) | B/F/2 | Ethanol | 4 |
| DAS | B/F/3 | Ethanol | 0 |
| 1-0469 (No: 1) | B/F/4 | Ethanol | 3 |
| GAP | B/F/5 | Ethanol | 4 |
| UPP-222 (No:2) | B/G/2 | Ethanol | 3 |

Example 4: Determination of Phytase Activity of Transformants

The level of phytase activity was determined in the various transformants. Agar medium on plates was supplemented with 100 mM phosphate buffer, pH 6.5, and calcium phytate. The activity of phytase acts to convert the non-transparent colloid calcium phytate substance into transparent material, forming a transparent halo around colonies expressing and secreting a phosphatase (phytase). An increased expression of the phytase by the cells leads to increased secretion of the enzyme, as demonstrated by a wider halo observed around the cell colony. Reporter activity was demonstrated with the UPP and Chr1-0469 promoters (FIG. 10). In FIG. 10, the transformants harboring promoter sequences GAP, Chr1-0469 promoter (SEQ ID NO: 1) and the UPP promoter (SEQ ID NO: 2) are cloned upstream of the ORF consisting of the *S. cerevisiae* pre-pro alpha factor fused in frame with DNA encoding the *E. coli* appA2 phytase. Cells were spotted on diagnostic plates with calcium phytate and either glucose or methanol and incubated for 27 hours at 30° C. The level of phytase expression with the promoters is noted by 0, +1, +2, +3, +4, and +5, with the level of expression increasing from 0 to +5. The relative levels of phytase expression are shown in the table below with No:1 and No:2 representing SEQ ID NO: 1 and SEQ ID NO: 2, respectively.

TABLE X

Relative Phytase Activity from FIG. 10

| Promoter (seq: ID) | Carbon Source | Relative activity 1-5 (5 is highest activity) |
|---|---|---|
| GAP | glucose | 2 |
| No: 1 | glucose | 2 |
| No: 2, c | glucose | 5 |
| No: 2, d | glucose | 5 |
| No: 2, e | glucose | 5 |
| GAP | methanol | 1 |
| No: 1 | methanol | 2 |
| No: 2, c | methanol | 2 |
| No: 2, d | methanol | 2 |
| No: 2, e | methanol | 2 |

What is claimed is:

1. An isolated nucleic acid wherein the sequence of the isolated nucleic acid comprises a sequence at least 95% identical to SEQ ID NO:2, or at least 95% identical to a fragment thereof, wherein the isolated nucleic acid comprises the sequence of a constitutive *Pichia pastoris* promoter operably linked to a heterologous coding sequence, and wherein the fragment extends about 300 nucleotides, about 400 nucleotides, about 500 nucleotides, about 600 nucleotides, or about 700 nucleotides upstream from the 3' end of SEQ ID NO:2, wherein the fragment is a continuous fragment of SEQ ID NO:2 and wherein the fragment comprises a TATA box sequence to direct initiation of transcription.

2. The isolated nucleic acid of claim 1 wherein the sequence of the isolated nucleic acid is at least 98% identical to SEQ ID NO:2, or at least 98% identical to the fragment thereof.

3. The isolated nucleic acid sequence of claim 1 wherein the sequence of the isolated nucleic acid is SEQ ID NO:2, or the fragment thereof.

4. The isolated nucleic acid of claim 1 wherein the heterologous coding sequence encodes a protein selected from the group consisting of a toxin, an antibody, a hormone, an enzyme, a growth factor, a cytokine, a structural protein, an immunogenic protein, and a cell signaling protein.

5. The isolated nucleic acid of claim 4 wherein the protein is an enzyme for use in animal feed.

6. The isolated nucleic acid of claim 5 wherein the protein is selected from the group consisting of a mannanase, an amylase, a glucanase, a protease, a cellulase, and a xylanase.

7. The isolated nucleic acid of claim 5 wherein the protein is a phytase.

8. The isolated nucleic acid of claim 5 wherein the protein is a galactosidase.

9. A host cell comprising the isolated nucleic acid of claim 1.

10. An expression vector comprising the isolated nucleic acid of claim 1.

11. A host cell comprising the expression vector of claim 10.

12. The host cell of claim 11 wherein the host cell is a *Pichia* species.

13. The host cell of claim 12 wherein the *Pichia* species is *Pichia pastoris*.

14. A DNA construct comprising the isolated nucleic acid of claim 1.

15. A method of producing a protein, the method comprising the step of culturing in a culture medium a host cell comprising a first expression cassette comprising the isolated nucleic acid of claim 1 wherein the heterologous coding sequence encodes a protein, wherein the culturing is done under conditions permitting expression of the protein.

16. The method of claim 15 wherein the protein is selected from the group consisting of a toxin, an antibody, a hormone, an enzyme, a growth factor, a cytokine, a structural protein, an immunogenic protein, and a cell signaling protein.

17. The method of claim 16 wherein the protein is an enzyme for use in animal feed.

* * * * *

SEQUENCE LISTING

```
<160> NUMBER OF SEQ ID NOS: 13

<210> SEQ ID NO 1
<211> LENGTH: 1003
<212> TYPE: DNA
<213> ORGANISM: Pichia pastoris
```

-continued

<400> SEQUENCE: 1

```
tgccaggatc tgaccactac aagaagcgta attaagtatt tattatgtag cttgaggaat      60
tgatttctaa aggccaaaga tgatgtagag caatagtaga gtgattagca agtttctgaa     120
catgttttgt ggtcgggtat taggcgccgt acctctgtat ttttttttt tggcagatgg     180
gatgaccact gtgcttacat aattttcgat gggccctttt ggaaacgacc actccttccg     240
atcacgtaat actaggcgag tatcactacg cgtcggtatc cgcattttag ccgctttaac     300
gacaaggtca gggtaaatac tgtgttgcat gggcgatgcc gtaggatctg gccaacttgg     360
aacagagcag cccaccgcgt aggcagcgct tgggaccagt ttgttagcca atcagttccc     420
ccgtctgagt ccctacacgc tcaggcttgc atggatatgc atgaaaaatg tcaactcagt     480
cgcacacagg gatgctgttg tcgtggtgag aaaaagctaa aatagcaaac ccatagcaat     540
cgagagactg tgattggaag caaaagaacc aggcattgac taggaaagac tgacaagaaa     600
attagacggt gccagtggta tttcattgaa ttgcactgaa cacgcctccc atttccttcc     660
ctcaatccat tcaaagggct aattaaacct tatctcggcc tacattagtt gtcatggaaa     720
cgtctcactt tctctctgtg tcccacagta gcgagtaggc ggagagacca aaaatggtct     780
ctcggcccta atcaaaacat cctttgtcgc gttgttttca gatcgattcg caatctgaga     840
gaaaaacaat aacaccaaaa taaaaagctt ggaaaaagaa gacatgattc acatccacta     900
gtaaaatata aatactcctg ccgcctcccc ctttcctttc ttcttattcc tcaactcact     960
gtttcagttt attccaacta ctttcactca cttatcaaaa atg                      1003
```

<210> SEQ ID NO 2
<211> LENGTH: 773
<212> TYPE: DNA
<213> ORGANISM: Pichia pastoris

<400> SEQUENCE: 2

```
gggtgaaagc caaccatctt tgtttcgggg aaccgtgctc gccccgtaaa gttaattttt      60
ttttcccgcg cagctttaat ctttcggcag agaaggcgtt ttcatcgtag cgtgggaaca     120
gaataatcag ttcatgtgct atacaggcac atggcagcag tcactatttt gctttttaac     180
cttaaagtcg ttcatcaatc attaactgac caatcagatt ttttgcattt gccacttatc     240
taaaaatact tttgtatctc gcagatacgt tcagtggttt ccaggacaac acccaaaaaa     300
aggtatcaat gccactaggc agtcggtttt atttttggtc acccacgcaa agaagcaccc     360
acctctttta ggttttaagt tgtgggaaca gtaacaccgc ctagagcttc aggaaaaacc     420
agtacctgtg accgcaattc accatgatgc agaatgttaa tttaaacgag tgccaaatca     480
agatttcaac agacaaatca atcgatccat agttacccat tccagccttt tcgtcgtcga     540
gcctgcttca ttcctgcctc aggtgcataa ctttgcatga aaagtccaga ttagggcaga     600
ttttgagttt aaaataggaa atataaacaa atataccgcg aaaaaggttt gtttatagct     660
tttcgcctgg tgccgtacgg tataaataca tactctcctc ccccccctgg ttctcttttt     720
cttttgttac ttacatttta ccgttccgtc actcgcttca ctcaacaaca aaa            773
```

<210> SEQ ID NO 3
<211> LENGTH: 939
<212> TYPE: DNA
<213> ORGANISM: Pichia pastoris

<400> SEQUENCE: 3
gatctaacat ccaaagacga aaggttgaat gaaacctttt tgccatccga catccacagg 60
tccattctca cacataagtg ccaaacgcaa caggagggga tacactagca gcagaccgtt 120
gcaaacgcag gacctccact cctcttctcc tcaacaccca cttttgccat cgaaaaacca 180
gcccagttat tgggcttgat tggagctcgc tcattccaat tccttctatt aggctactaa 240
caccatgact ttattagcct gtctatcctg gcccccctgg cgaggttcat gtttgtttat 300
ttccgaatgc aacaagctcc gcattacacc cgaacatcac tccagatgag ggctttctga 360
gtgtggggtc aaatagtttc atgttcccca aatggcccaa aactgacagt ttaaacgctg 420
tcttggaacc taatatgaca aaagcgtgat ctcatccaag atgaactaag tttggttcgt 480
tgaaatgcta acggccagtt ggtcaaaaag aaacttccaa aagtcggcat accgtttgtc 540
ttgtttggta ttgattgacg aatgctcaaa aataatctca ttaatgctta gcgcagtctc 600
tctatcgctt ctgaaccccg gtgcacctgt gccgaaacgc aaatggggaa acacccgctt 660
tttggatgat tatgcattgt ctccacattg tatgcttcca agattctggt gggaatactg 720
ctgatagcct aacgttcatg atcaaaattt aactgttcta acccctactt gacagcaata 780
tataaacaga aggaagctgc cctgtcttaa accttttttt ttatcatcat tattagctta 840
ctttcataat tgcgactggt tccaattgac aagcttttga ttttaacgac ttttaacgac 900
aacttgagaa gatcaaaaaa caactaatta ttcgaaacg 939

<210> SEQ ID NO 4
<211> LENGTH: 1001
<212> TYPE: DNA
<213> ORGANISM: Pichia pastoris

<400> SEQUENCE: 4
catgttggta ttgtgaaata gacgcagatc gggaacactg aaaaataaca gttattattc 60
gagatctaac atccaaagac gaaaggttga atgaaacctt tttgccatcc gacatccaca 120
ggtccattct cacacataag tgccaaacgc aacaggaggg gatacactag cagcagaccg 180
ttgcaaacgc aggacctcca ctcctcttct cctcaacacc cacttttgcc atcgaaaaac 240
cagcccagtt attgggcttg attggagctc gctcattcca attccttcta ttaggctact 300
aacaccatga ctttattagc ctgtctatcc tggcccccct ggcgaggttc atgtttgttt 360
atttccgaat gcaacaagct ccgcattaca cccgaacatc actccagatg agggctttct 420
gagtgtgggg tcaaatagtt tcatgttccc caaatggccc aaaactgaca gtttaaacgc 480
tgtcttggaa cctaatatga caaaagcgtg atctcatcca agatgaacta agtttggttc 540
gttgaaatgc taacggccag ttggtcaaaa agaaacttcc aaaagtcggc ataccgtttg 600
tcttgtttgg tattgattga cgaatgctca aaaataatct cattaatgct tagcgcagtc 660
tctctatcgc ttctgaaccc cggtgcacct gtgccgaaac gcaaatgggg aaacacccgc 720
tttttggatg attatgcatt gtctccacat tgtatgcttc caagattctg gtgggaatac 780
tgctgatagc ctaacgttca tgatcaaaat ttaactgttc taacccctac ttgacagcaa 840
tatataaaca gaaggaagct gccctgtctt aaaccttttt ttttatcatc attattagct 900
tactttcata attgcgactg gttccaattg acaagctttt gattttaacg acttttaacg 960
acaacttgag aagatcaaaa aacaactaat tattcgaaac g 1001

<210> SEQ ID NO 5
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 5

atccctacac gctcaggctt                                              20


<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 6

nnnggtctcn atcctcgctg ggtgaaagcc aac                               33


<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 7

nnnggtctcn atccgcagat acgttcagtg gtttcc                            36


<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 8

nnnggtctcn atccagtacc tgtgaccgca attc                              34


<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
```

<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 9
nnnggtctcn atcctgcctc aggtgcataa ctt 33

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 10
nnnggtctcn atccaatgga ccaaattgtt gcaaggt 37

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)
<223> OTHER INFORMATION: a, c, t, g, unknown or other

<400> SEQUENCE: 11
nnnggtctcc atccctttgt tgagcaaca 29

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)
<223> OTHER INFORMATION: a, c, t, g, unknown or other

<400> SEQUENCE: 12
nnnggtctcg atccgcccaa acgaacag 28

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(3)

-continued

```
<223> OTHER INFORMATION: a, c, t, g, unknown or other

<400> SEQUENCE: 13

nnnggtctcc atccaaagac gaaaggttga atga                              34
```